(12) United States Patent
Ogura et al.

(10) Patent No.: US 6,502,984 B2
(45) Date of Patent: **\*Jan. 7, 2003**

(54) RADIOGRAPHIC APPARATUS

(75) Inventors: Takashi Ogura, Utsunomiya (JP); Keiichi Kawasaki, Tokyo (JP); Akira Hirai, Utsunomiya (JP)

(73) Assignee: Canon Kabushiki Kaisha, Tokyo (JP)

(\*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/008,510

(22) Filed: Jan. 16, 1998

(65) Prior Publication Data

US 2001/0012330 A1 Aug. 9, 2001

(30) Foreign Application Priority Data

Jan. 17, 1997 (JP) ................................ 9-006388
Jan. 17, 1997 (JP) ................................ 9-019941

(51) Int. Cl.[7] .............................................. G01N 23/04
(52) U.S. Cl. ......................................... 378/206; 378/63
(58) Field of Search ............................. 378/206, 62, 63

(56) References Cited

U.S. PATENT DOCUMENTS

| | | | | | |
|---|---|---|---|---|---|
| 4,246,607 A | \* | 1/1981 | Vijverberg | .................... | 378/63 |
| 4,907,252 A | \* | 3/1990 | Aichinger et al. | .......... | 378/206 |
| 4,969,177 A | \* | 11/1990 | Otsuke et al. | .............. | 378/206 |
| 5,539,798 A | | 7/1996 | Asahina et al. | ............ | 378/98.5 |

\* cited by examiner

*Primary Examiner*—Craig E. Church
(74) *Attorney, Agent, or Firm*—Fitzpatrick, Cella, Harper & Scinto

(57) ABSTRACT

This invention relates to a radiographic apparatus which comprises a radiographic image photographing unit for photographing a radiographic image of an object irradiated with radiation by a radiation generating device, a distance measuring system for measuring the distances or distance from the radiation generating device to the radiographic image photographing unit and/or the object, and distance information indicating means for indicating distance information obtained by the distance measuring system.

13 Claims, 31 Drawing Sheets

RADIOGRAPHIC APPARATUS

BACKGROUND OF THE INVENTION

1. Field of the Invention

The present invention relates to a radiographic apparatus for photographing a radiographic image of an object in the medical field or nondestructive inspection field.

2. Related Background Art (1) FIG. 1 is a diagram of a conventional radiographic apparatus. A radiographic image photographing means 302 for photographing a transmitted radiographic image of an object S is disposed in front of a radiation generating means 301 as a radiation source for generating radiation. The radiation generating means 301 and radiographic image photographing apparatus 302 irradiate radiation and photograph an image of the object S on the basis of the photographing conditions, e.g., the tube voltage or tube current for an X-ray tube as the radiation source, irradiation time, and the like, set by the operator using a photographing condition setting means 303.

(2) In X-ray radiography, X-rays that have scattered inside an object largely influence the image. In order to efficiently remove scattered X-rays, a scattered X-ray removing grid (to be simply referred to as a grid hereinafter) is used to help improve the contrast and sharpness of an X-ray image. The grid used can be classified into a parallel grid and convergence grid depending on their structures. FIG. 2 is a sectional view of the parallel grid, in which copper foils 391 and intermediate substances 390 are disposed to be parallel to each other and in a direction perpendicular to incoming X-rays. FIG. 3 is a sectional view of the convergence grid, in which copper foils 391 and intermediate substances 390 are disposed to converge at a single point (in this case, a convergence point 401). The intermediate substance consists of aluminum, wood, or the like.

(3) Conventional radiography uses a system as a combination of a film and intensifying paper. In recent years, along with the development of computers, various types of digital image photographing apparatuses have been developed and are used in clinical applications. A photographing apparatus using a photostimulable phosphor sheet as one of such apparatuses temporarily records a radiographic image of an object S on a photostimulable phosphor sheet, and then irradiates excitation light such as a laser beam onto that photostimulable phosphor sheet to cause stimulated emission. Based on an image signal obtained by photoelectrically reading the emitted light, a radiographic image of the object S is printed on a silver halide film or is displayed on a CRT display.

On the other hand, a photographing apparatus using a photodetection array converts a radiographic image of the object S into a visible image via a scintillator or image intensifier, converts that visible image into an image signal via the photodetection array, and prints or displays the radiographic image of the object on a silver halide film or CRT display.

(4) Furthermore, in radiography in the medical field, in order to obtain a high-quality image without re-photographing, the radiographic conditions must be set to match the state and characteristics of the object S. That is, the field of irradiation, quality, and exposure dose of radiation must be optimized, and appropriate image processes are required for a digital radiographic image to make it easier to see.

FIG. 4 shows the arrangement of a radiographic apparatus according to the third conventional art. When a radiation generating means 301 irradiates radiation onto an object S, the radiation is intensity-modulated and scattered in accordance with the internal structure of the object S owing to interactions such as absorption, scattering, and the like of the object S with respect to the radiation, and then reaches a radiographic image photographing means 302 to obtain a radiographic image. Note that a grid 304 disposed in front of the radiographic image photographing means 302 removes scattered radiation to improve the contrast of the radiographic image.

In general, the radiographic image photographing means 302 comprises a phosphor $CaWO_4$ or the like that produces luminescence at an intensity proportional to the exposure dose, and a silver halide film, and the image of the object S is recorded on the film as a latent image. After development, the recorded image is presented as a visible image that gives a density proportional to the logarithm of the luminescence amount, and is used in diagnosis, inspection, and the like.

Also, a computed radiography (CR) apparatus using an imaging plate applied with a BaFBr:Eu phosphor and BaF:Eu phosphor which produce photostimulated luminescence is also used. The CR apparatus temporarily records a radiographic image of the object S on the imaging plate, and then irradiates excitation light such as a laser beam onto the imaging plate to cause stimulated emission. The apparatus prints or displays the radiographic image of the object S on a silver halide film or CRT display on the basis of an image signal obtained by photoelectrically reading the emitted light.

Furthermore, recently, a technique for reading a digital image using, as the radiographic image photographing means 302, a photoelectric conversion device on which pixels each consisting of a very small photoelectric conversion element, switching element, and the like are arranged in a lattice pattern, has been developed.

(5) It is important in radiography to obtain a high-quality image without re-photographing, and optimal radiographic conditions must be selected in correspondence with the state and characteristics of the object S and those of the radiographic apparatus. That is, the field of irradiation must be stopped down, and the dose and quality of radiation must be optimized. Furthermore, when a radiographic image is to be digitally processed, posture determination, edge extraction, and the like of the object S are required.

In order to stop down the field of irradiation, a lead aperture stop is conventionally inserted immediately after the radiation generation device, and is manually moved. In order to confirm the divergence of radiation, a visible light source is arranged at a position conjugate with the radiation generating means 301, and the operator visually checks the degree of eclipse of the projected light by the aperture stop. In addition, in an X-ray radiography apparatus, the irradiation range is confirmed in advance using a television monitor.

Upon setting the dose and quality of radiation, the photographer sets them by determining proper conditions on the basis of the posture and photographing portion of the object S, or inputs information associated with the posture and the photographing portion of the object S to the apparatus, which automatically sets proper conditions.

(a) However, in conventional art (1) above, since the operator must set optimal photographing conditions to obtain a radiographic image which is easy to observe, he or she must change the positional relationship between the radiation generating means 301 and radiographic image photographing means 302 depending on the photographing method used, and must measure the distance between them using a scale in every change. Furthermore, before the operator gains experience in using the apparatus, e.g., immediately after installation of the photographing apparatus, he or she must create an irradiation condition table or the like and must photograph with reference to that table. Upon creating the irradiation condition table, the operator must make physical contact with a patient as the object S to directly measure the breast thickness using a tool such as a breast meter or the like.

(b) When the grid described in conventional art (2) is used, grid cutoff occurs. FIG. 5 shows the case wherein grid cutoff has occurred due to the parallel grid, and illustrates an X-ray tube focal point F, and shadow images 414a and 414b on an image receiving surface 413 obtained when X-rays are transmitted through lead foils 412a and 412b of a grid 411. The lead foils 412a is projected as a shadow image broader than that of the lead foil disposed in the direction of primary X-rays, which do not reach the image receiving surface accordingly. As a consequence, in an X-ray image, a portion where the broader shadow image is formed becomes darker than a portion where it is not formed. The grid cutoff amount normally becomes larger as the grid ratio is higher and the distance between the grid and X-ray tube focal point F is shorter.

Even when the convergence grid is used, if the positional relationship between the X-ray tube focal point F and a convergence point 401 of the grid is not proper, grid cutoff takes place. FIG. 6 shows an example wherein the X-ray tube focal point F deviates horizontally from the convergence point 401. In this case, since all the lead foils of the grid cause equal grid cutoff of primary X-rays, an entirely and evenly dark X-ray image is obtained.

The grid is classified into a still grid and moving grid depending on their use methods. The still grid is used in the still state with respect to an X-ray image receiving surface (to be simply referred to as an image receiving surface hereinafter), and the moving grid is built and used in a device for moving the grid relative to the image receiving surface to remove shadow images of the lead foils.

Even in a conventional apparatus using the moving grid, since the moving speed of the grid is constant, the grid does not move at equal intervals about the center of the field of X-ray irradiation during the X-ray irradiation time, and the same result as that obtained by integrating the horizontal deviation state within the irradiation time is obtained, i.e., a density pattern is formed in an X-ray image. On the other hand, when the photographing time is long and the grid must be reciprocally moved, shadow images of the lead foils are often formed at the turning point positions.

(c) In conventional art (3) above, an apparatus which comprises image process means for outputting an image with an optimal density and contrast when overexposure or underexposure has occurred due to condition setting errors upon photographing, or an apparatus which comprises determination means for determining the photographing posture, photographing portion, and field of irradiation of the object S to optimally execute such image process is known. However, since the radiographic image of the object S is used in such determination, the image size is as large as 1024×1024 samples and 12 bits required for quantization, thus requiring a long arithmetic time. Also, under the influences of scattered radiation, it is hard to accurately execute pattern matching of the object S and recognition of the field of irradiation.

(d) In conventional art (4) above, in order to stop down the field of irradiation of radiation coming from the radiation generating means 301, a movable radiation aperture stop 305 inserted immediately before the radiation generating means 301 is manually adjusted. Furthermore, a light source 306 is arranged at a position conjugate with the radiation generating means 301, and the operator confirms the field of irradiation by visually observing the degree of eclipse of the projected light by the movable radiation aperture stop 305. In this case, the operator must stand at the side of the radiation generating means 301, and must adjust the width of the movable radiation aperture stop 305 every time the object S changes, thus requiring very troublesome operations. Especially, in case of breast photographing, since front and side images of an identical object S must be alternately photographed, the operator must adjust the width of the aperture stop in each photographing. Owing to such tedious operations, the operator may often photograph a side image with a small width without stopping down the movable radiation aperture stop 305.

However, when the side image of the object S is photographed without stopping down the movable radiation aperture stop 305, i.e., in the full-open state, radiation also reaches an ineffective photographing region, and so-called unintercepted radiation, which is not absorbed by the human body, directly reaches a photo-timer light-receiving unit 307 used for automatically controlling the dose. Hence, the unintercepted radiation increases detection errors of the dose, and the dose cannot be normally detected.

Normally, the front and side images of the breast portion must be photographed with different radiation qualities. However, at present, the operator must visually confirm the posture of the object and switch the radiation tube voltage at the console of the radiation generation device to photograph the front and side images of the breast portion.

In the radiography apparatus combining a radiation image intensifier and television camera, since radiographic observation is done on the television monitor prior to film photographing, the radiation range can also be visually confirmed. In this case, the operator need not stand at the side of the radiation generating means, and can also adjust the aperture stop by remote control. However, when the object region is to be extracted from the radiographic image of the object to automate aperture stop adjustment, the edges blur under the influences of scattered radiation and the like, thus making region extraction difficult. In addition, the object S is kept irradiated with radiation even during radiographic observation.

On the other hand, in the CR apparatus using the imaging plate, the signal level is detected by a coarse scan called a pre-scan using a very weak laser beam, so as to extract the object region, thereby optimizing the scan conditions for a main scan. However, since such processes are done after photographing the object S, they are not helpful in optimizing the photographing itself. Also, it is very hard to extract the object region under the influences of scattered radiation and the like as in the radiographic apparatus.

As described above, upon setting the photographing conditions and the like for the radiographic apparatus, the operator visually observes the object S, stops down the field of irradiation in correspondence with the size of the object S, adjusts the radiation quality in accordance with front and side shots, and manually switches the gain of a photo-timer.

However, since the radiographic apparatus depends on the operator to acquire information for recognizing the state and characteristics of the object S, it is especially difficult for the apparatus to accurately recognize the object region. The operator may often omit some setting operations in units of objects S, e.g., operation for stopping down the field of irradiation, to reduce his or her work loads. As a consequence, an image with inappropriate image quality may be obtained. For example, when radiation is irradiated even to an ineffective photographing region, the photo-timer produces recognition errors under the influences of unintercepted radiation, and a desired dose is not given. As a result, an effective radiographic image cannot often be obtained. Since the amount of radiation that reaches the human body differs depending on a front image in which the object S becomes thin or a side image in which the object S becomes thick, an effective radiographic image cannot be obtained unless the quality of radiation is switched, resulting in unnecessary radiation.

(e) In conventional art (5) above, in a photographing site with shorter photographing cycles, e.g., in group diagnosis, it is cumbersome to adjust the position of a lead aperture stop every time the object S changes. Especially, in breast photographing, the front and side images of one object S must often be alternately photographed, and adjustment must be done in each photographing. For this reason, photographing is often done with the aperture stop fully open. When a side image with a small width of the object S is photographed in such state, detection errors of the photo-timer of an automatic exposure means for automatically controlling the radiation dose increase under the influence of unintercepted radiation that is not absorbed by the human body, and an appropriate radiation dose often cannot be obtained. As a result, since sufficient object information cannot be obtained from the acquired image, photographing must be re-done.

Furthermore, although the radiation quality to be manually set must be optimized to improve image quality, since the optimal conditions vary depending on different portions, postures, and the like of the object, it is very cumbersome to set the quality in units of objects as in the lead aperture stop. For this reason, all objects are often photographed under identical conditions. Also, since the amount of scattered rays that reach the human body differs depending on the object postures in front and side shots, the gain of the photo-timer must be switched to obtain an effective radiographic image. In either case, improper photographing may result.

(f) In these conventional arts, it is consequently difficult to accurately photograph in correspondence with the object.

SUMMARY OF THE INVENTION

It is the first object of the present invention to provide a radiographic apparatus which can solve the problems in conventional art (a) above, and can shorten the operation time by simplifying cumbersome operations that must be done by the operator.

It is the second object of the present invention to provide an X-ray photographing apparatus which determines the X-ray irradiation time by measuring the body thickness of an object before X-ray irradiation, and controls the moving grid on the basis of the determined X-ray irradiation time information to remove the influences of shadow images of lead foils formed in an X-ray image.

It is the third object of the present invention to provide a radiographic apparatus which can solve problems (c) in the above-mentioned conventional art, and can output an optimal image at high speed by performing image processes of a radiographic image.

It is the fourth object of the present invention to provide a radiographic apparatus which can solve problems (d) in the above-mentioned conventional art, and determines optimal photographing conditions by easily acquiring two-dimensional information of the object required for setting parameters for image processes of a radiographic image.

It is the fifth object of the present invention to provide a radiographic apparatus which can solve problems (e) in the above-mentioned conventional art, and can execute optimal radiography by acquiring object information immediately before photographing and reflecting it in setting of the photographing conditions.

It is the sixth object of the present invention to provide a radiographic apparatus which can execute appropriate radiography accurately corresponding to the situation of each object.

DESCRIPTION OF THE PREFERRED EMBODIMENTS

The present invention will be described in detail hereinafter by way of its embodiments illustrated in FIGS. 7 to 47A and 47B.

Figure 7:
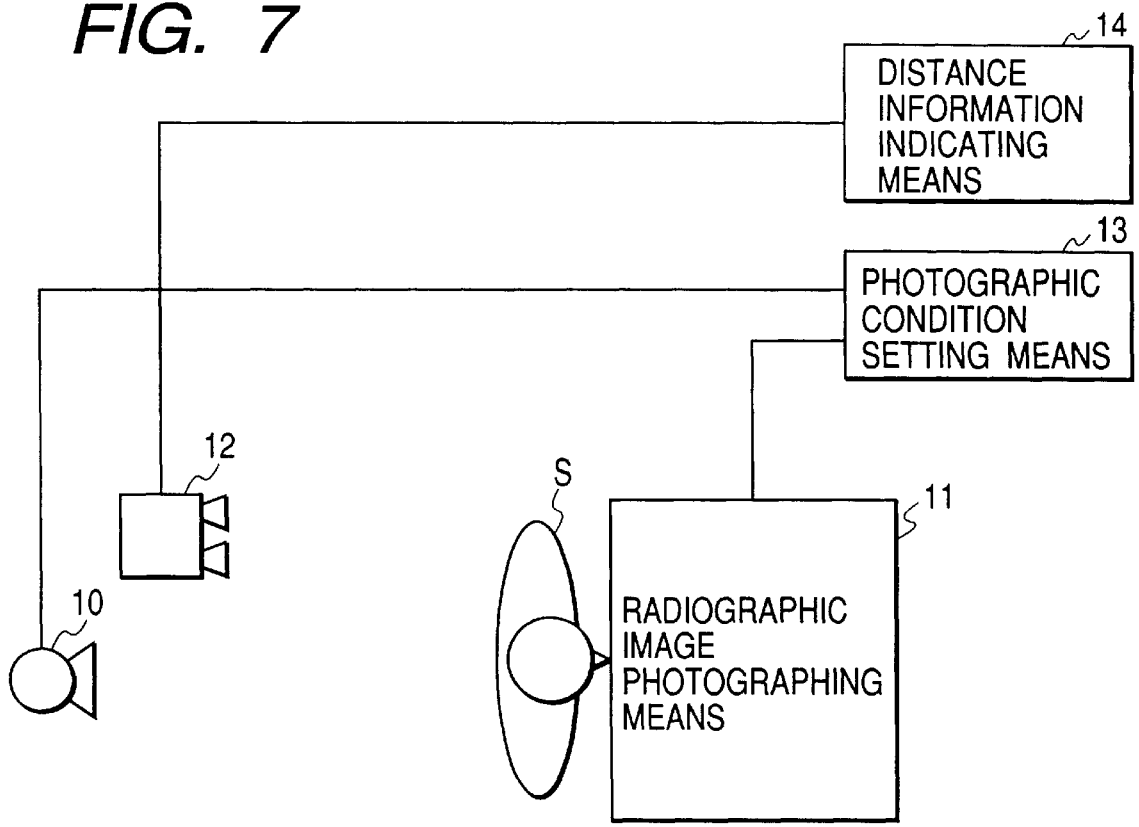
FIG. 7 is a diagram showing the arrangement according to the first embodiment of the present invention.

FIG. 7 is a diagram of a radiographic apparatus according to the first embodiment. A radiographic image photographing means 11 for photographing a radiographic image of an object S via the object S is disposed in front of a radiation generating means 10 as a radiation source for generating radiation, and an automatic distance measuring means 12 for measuring the distances or distance from the radiation generating means 10 to the radiographic image photographing means 11 and/or the object S in a non-contact manner is disposed in the vicinity of the radiation generating means 10.

The output from a photographic or photographing condition setting means 13, at which the operator controls irradiation by setting the photographing conditions such as a tube voltage, tube current, irradiation time, and the like of an X-ray tube as the radiation source, is connected to the radiation generating means 10, and the output from the radiographic image photographing means 11 is connected to the photographing condition setting means 13. The output from the automatic distance measuring means 12 is connected to a distance information indicating means 14 that indicates distance information.

The object S as a patient is located in front of the radiographic image photographing means 11, and the operator sets various photographing conditions at the photographing condition setting means 13. Radiation coming from the radiation generating means 10 is transmitted through the object S and reaches the radiographic image photographing means 11, thus photographing a radiographic image of the object S. At this time, the automatic distance measuring means 12 measures the distances or distance from the radiation generating means 10 to the radiographic image photographing means 11 and/or the object S in a non-contact manner, and presents the distance information to the distance information indicating means 14.

Figure 8:
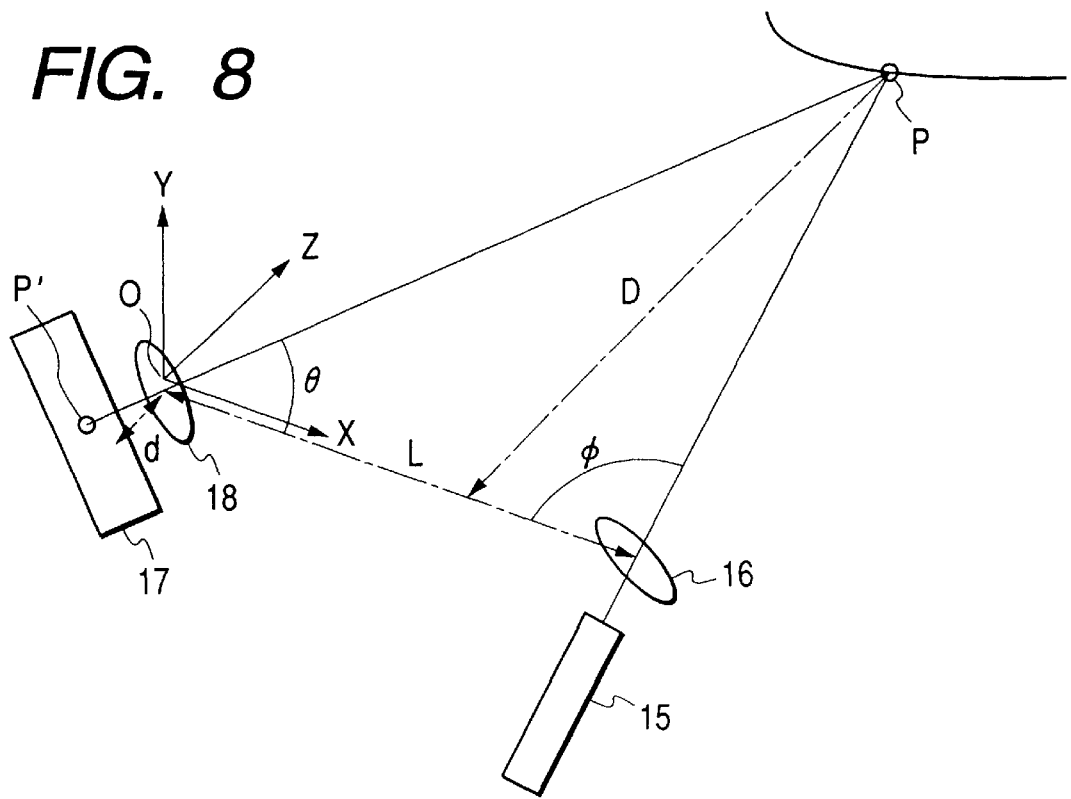
FIG. 8 is an explanatory view of automatic distance measurement.

FIG. 8 is an explanatory view of distance measurement by the automatic distance measuring means 12. The automatic distance measuring means 12 comprises a light source 15 such as an LED, LD, or the like, a projection optical system 16 for focusing a light beam coming from the light source 15 to form a beam spot P on the observation surface, a position detection element 17 such as a CCD, PSD, or the like, and an imaging optical system 18 for imaging a beam spot image P' on the position detection element 17.

A light beam emitted by the light source 15 is focused by the projection optical system 16, and forms a small beam spot P on the observation surface. The beam spot P is imaged on the position detection element 17 by the imaging optical system 18 to form a beam spot image P'. A relative distance Z from the beam spot image P on the observation surface to the automatic distance measuring means 12 can be calculated from the coordinate position of the beam spot image P' on the position detection element 17.

In FIG. 8, assume that the principal point of the imaging optical system 18 defines an origin O, the imaging plane of the position detection element 17 is set at a position of Z=−d, and the principal point of the projection optical system 16 is set at a position of X=L. When a beam spot image P formed on the observation surface by a light beam irradiated in a $\phi$ direction with respect to the origin O is observed from the origin O in a $\theta$ direction, a relative distance D to the beam spot image P is given by:

$$D = (L \times \tan\theta \times \tan\phi)/(\tan\theta + \tan\phi)$$

If x represents the coordinate position of the beam spot image P' on the position detection element 17, then the angle $\theta$ is given by:

$$\theta = \tan^{-1}(x/d)$$

The distance from the radiation generating means 10 to the radiographic image photographing means 11 is calculated from the above equation as the relative distance D by projecting the beam spot P onto the front surface of the radiographic image photographing means 11, e.g., a breast contact surface, and the distance from the radiation generating means 10 to the object S is calculated by the above equation as the relative distance D by projecting the beam spot P onto the surface of the object S.

Figure 9:
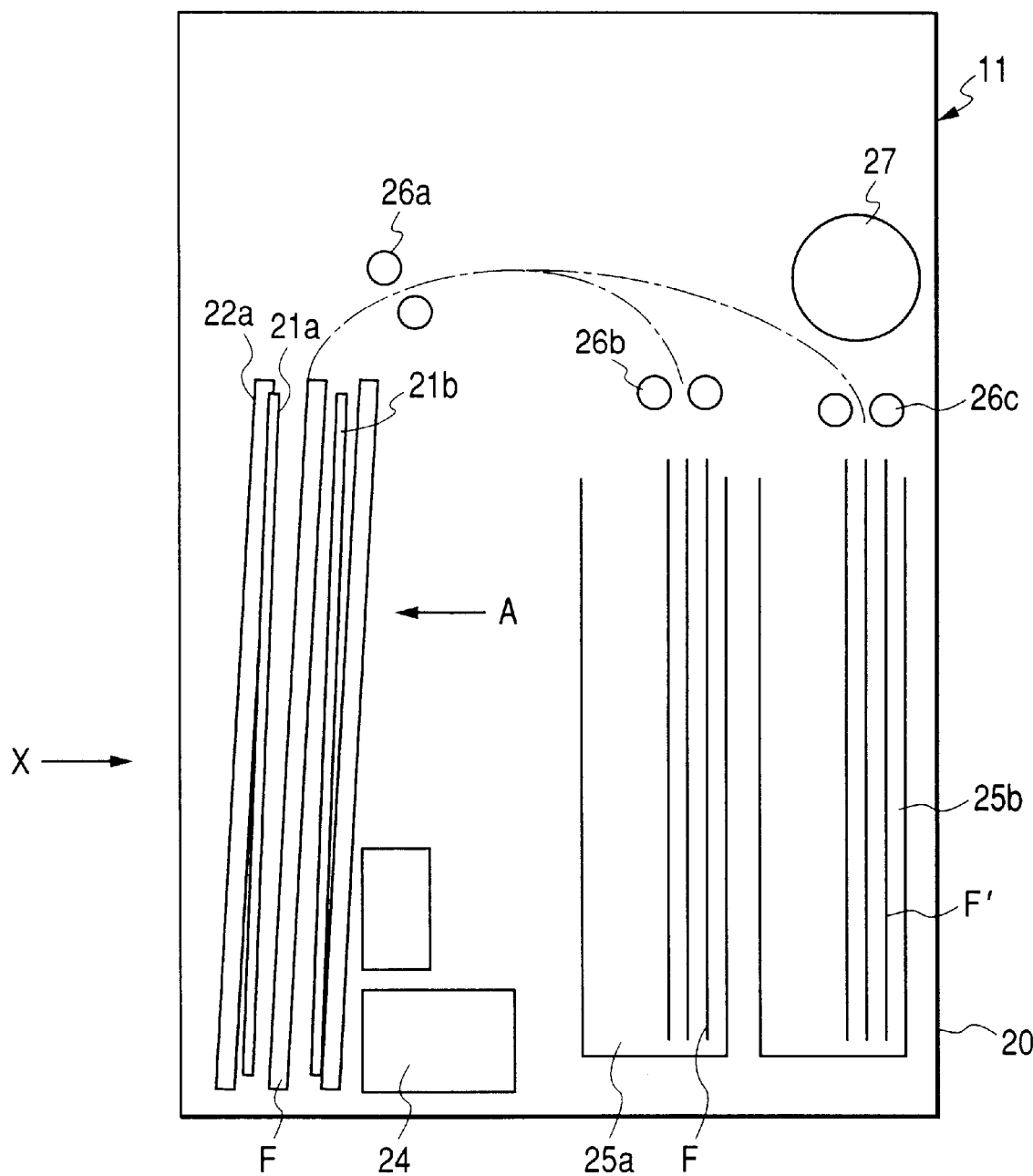
FIG. 9 is a sectional view of a radiographic image photographing means using a silver halide film.

FIG. 9 is a sectional view when an X-ray photographing film changer 20 is used as the radiographic image photographing means 11. Two film pressure plates 22a and 22b on the inner surfaces of which intensifying paper sheets 21a and 21b are adhered are disposed on the incoming side of radiation X. Upon photographing, a film F is sandwiched between the front and rear intensifying paper sheets 21a and 21b, and is tightly held by the front and rear film pressure plates 22a and 22b.

A radiation intensity detection means 23 for detecting the intensity of the radiation X transmitted through the film F, and a vacuum pump 24 are disposed behind these pressure plates, and a supply magazine 25a for storing unphotographed films F and a receive magazine 25b for storing photographed films F' are disposed behind the pump 24. Above these members, roller pairs 26a, 26b, and 26c for conveying an unphotographed film F from the supply magazine 25a to the photographing position and conveying a photographed film F' to the receive magazine 25b, and a motor 27 for driving these roller pairs 26a, 26b, and 26c are disposed.

Upon photographing using the film changer 20 with the above arrangement, the roller pairs 26a and 26b are driven by the motor 27 to pick up one film F from the unphotographed film storage supply magazine 25a, and feed it onto the front surface of the rear film pressure plate 22b adhered with the rear intensifying paper sheet 21b. The rear film pressure plate 22b is driven in the direction of an arrow A by a rear film pressure plate drive mechanism (not shown), and the film F is pressed against the front intensifying paper sheet 21a adhered on the front film pressure plate 22a. Furthermore, the film F is tightly held by vacuum between the front and rear intensifying paper sheets 21a and 21b upon operation of the vacuum pump 24. After the film F is completely tightly held between front and rear intensifying paper sheets 21a and 21b and is ready to be photographed, radiation is irradiated from the radiation generating means 10 upon operation of the operator, and a radiographic image of the radiation transmitted through the object S is photographed.

Furthermore, in the radiographic image photographing means 11, the radiation transmitted through the object S enters the radiation intensity detection means 23 which detects its intensity. The radiation intensity information is set in a look-up table making means (to be described later) and is used for making a look-up table.

Figure 10:
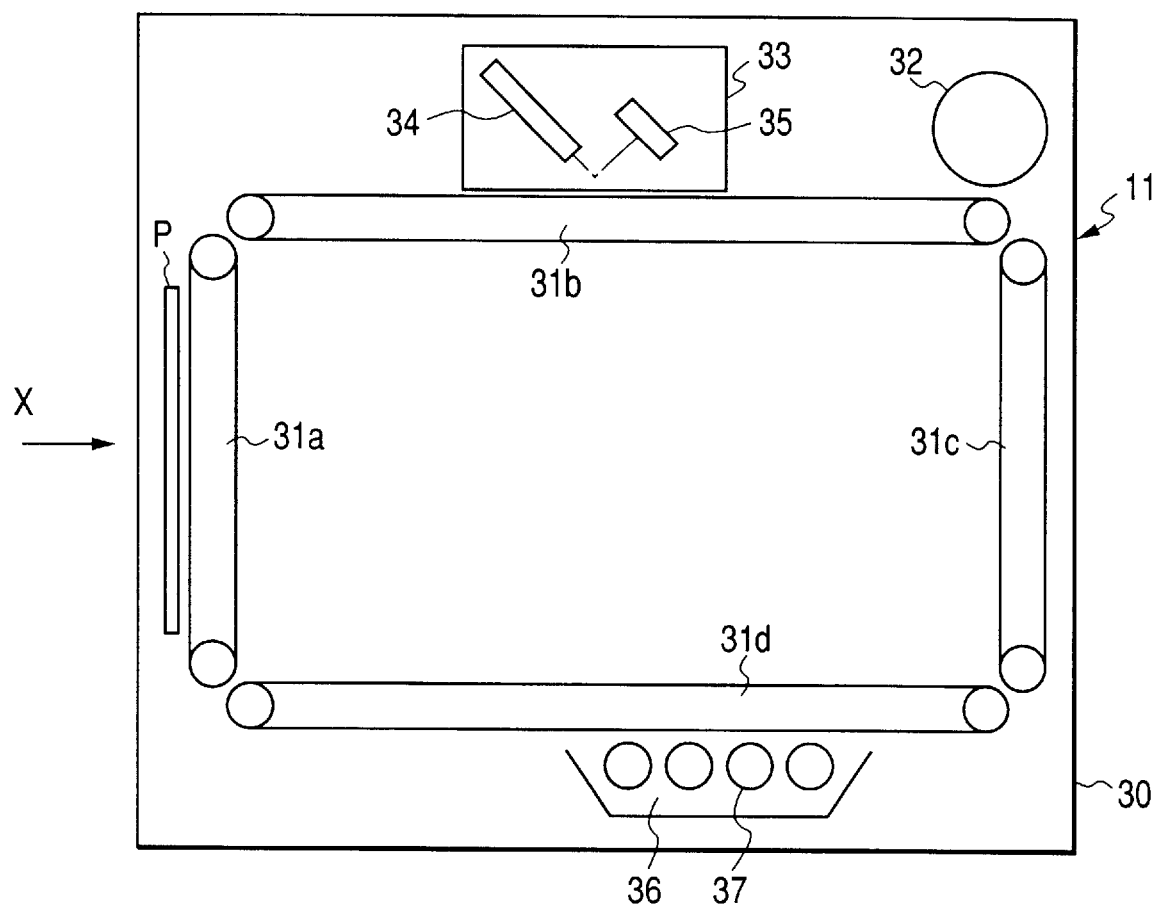
FIG. 10 is a sectional view of a radiographic image photographing means using a photostimulable phosphor.

FIG. 10 is a sectional view of the radiographic image photographing means 11 using a photostimulable phosphor sheet. This radiographic image photographing means uses a radiographic image information recording/reading device 30, which accumulates and records radiographic image information on a photostimulable phosphor sheet P, irradiates excitation light onto the sheet to read image information by detecting stimulated emission in accordance with the accumulated and recorded image information, and converts the image information into an electrical signal to reproduce an image.

In this radiographic image information recording/reading device 30, endless belts 31a, 31b, 31c, and 31d for conveying a photostimulable phosphor sheet P are disposed along the four sides of a rectangle, and are connected to a transmission mechanism including, e.g., chains, gears, and the like (not shown), and a motor 32 serving as a drive source. A reading means 35 is disposed in the vicinity of the endless belt 31b. The reading means 35 comprises a laser light source 33 and photomultiplier 34, and reads radiation information accumulated and recorded on the photostimulable phosphor sheet P. A quenching means 37 is disposed in the vicinity of the endless belt 31d. The quenching means 37 comprises a quenching light source 36 such as a fluorescent lamp, and the like, and makes the photostimulable phosphor sheet P emit residual energy.

The residual energy on the photostimulable phosphor sheet P is emitted by quenching light coming from the quenching light source 36 in the quenching means 37. After that, the motor 32 is driven by a control means (not shown) to drive the endless belts 31a to 31d via the transmission mechanism, thereby conveying the photostimulable phosphor sheet P to the radiation incident position. The photostimulable phosphor sheet P irradiated with radiation X at the endless belt 31a moves to the endless belt 31b where the reading means 35 is disposed. The laser light source 33 irradiates a laser beam onto the photostimulable phosphor sheet P, and stimulated emission having an intensity corresponding to the radiographic image information on the photostimulable phosphor sheet P is received by the photomultiplier 34. In this manner, the radiographic image information accumulated and recorded on the photostimulable phosphor sheet P is photoelectrically read. The radiographic image information is transferred to a look-up table making means (to be described later), and is used in making a look-up table. Also, the information is transferred to an image process means (not shown).

Figure 11:
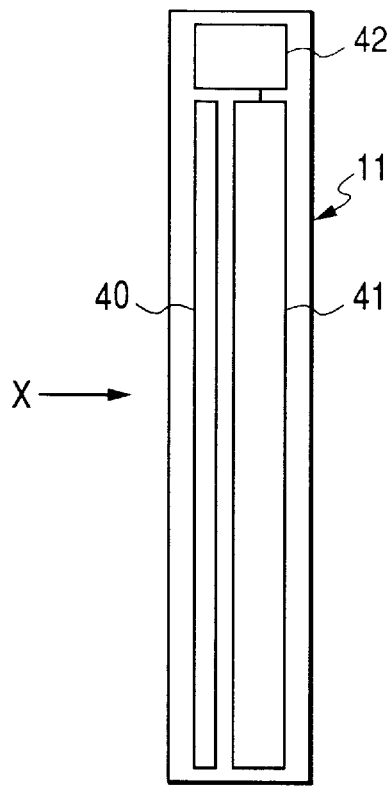
FIG. 11 is a sectional view of a radiographic image photographing means using a photodetection array.

FIG. 11 is a sectional view of the radiographic image photographing means 11 using a photodetector array. A scintillator 60 is disposed at the side of incoming radiation X, and a photodetector array 41 is disposed in the neighborhood of the scintillator 60. The output from a drive circuit 42 is connected to the photodetector array 41.

Upon incidence of radiation X, the scintillator 60 obtains luminescence in the visible range based on binding energy obtained when the host lattice of a phosphor is excited by high-energy X-rays and recombines. Note that this luminescence is produced by the lattice itself such as $CaWO_4$, $CdWO_4$, or the like, or by a luminescence center substance such as CsI:Tl, ZnS:Ag, or the like activated in the lattice. The drive circuit 42 drives the photodetector array 41 to convert photons into electrical signals to read out electrical signals from the individual pixels. The radiographic image information obtained by the drive circuit 42 is transferred to a look-up table making means (to be described later) and is used in making a look-up table. Also, the radiographic image information is transferred to an image process means (not shown).

Figure 12:
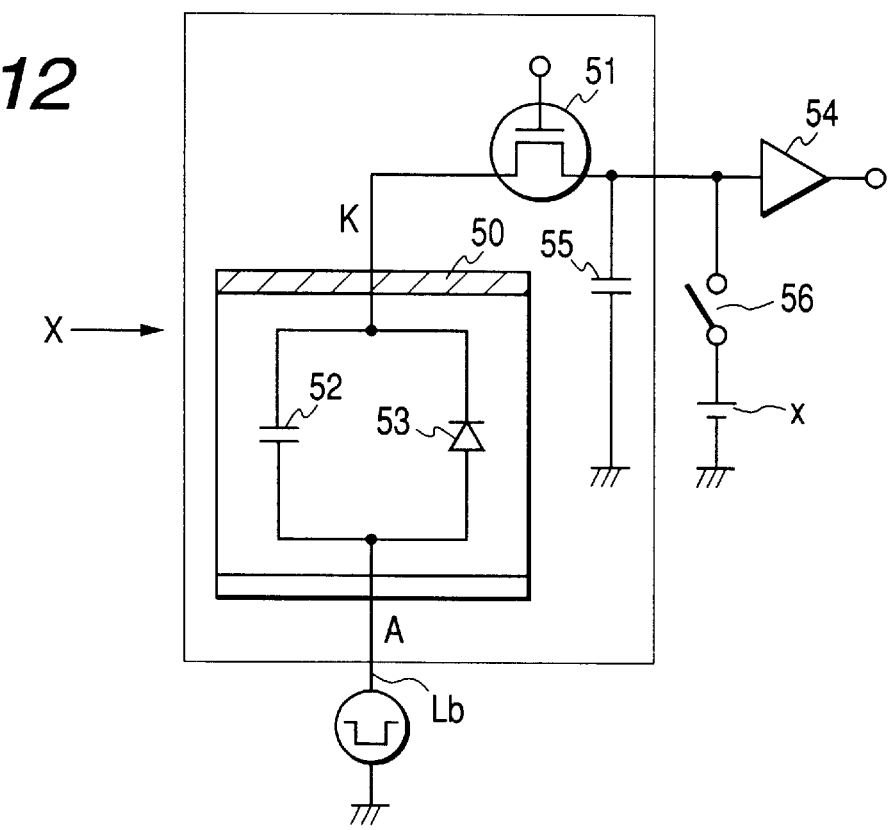
FIG. 12 is a diagram showing an electric circuit of a photodetection unit.

FIG. 12 shows the arrangement of the equivalent circuit of the photodetector array 41. In this circuit, a two-dimensional amorphous silicon sensor is used as a detection element. However, when other elements such as a solid-state imaging element such as a charge-coupled device, a photoelectric intensifier, and the like are used, the function and arrangement of the A/D converter remain the same.

One element in the photodetector array 41 is made up of a photodetection unit 50 and a switching TFT 51 for controlling accumulation and reading of a charge, and normally consists of amorphous silicon (αSi) formed on a glass substrate. A capacitor 52 in the photodetection unit 50 may simply comprise a photodiode having a parasitic capacitance, or may comprise a parallel circuit of a photodiode 53 and an additional capacitor 52 for improving the dynamic range of the detector.

The anode A of the photodiode 53 is connected to a bias wiring line Lb as a common electrode, and its cathode K is connected to the controllable switching TFT 51 used for reading out a charge accumulated on the capacitor 52. The switching TFT 51 is a thin film transistor connected between the cathode K of the photodiode 53 and a charge reading amplifier 54. A parallel circuit of a capacitive element 55 and a reset switching element 56 is connected between the switching TFT 51 and the amplifier 54.

The reset switching element 56 is enabled by the switching TFT 51 and the signal charge to reset the capacitor 52. After that a charge corresponding to the radiation dose is produced in the photodiode 53 upon receiving radiation, and is accumulated on the capacitor 52. The reset switching element 56 is enabled again by the switching TFT 51 and the signal charge to transfer the charge to the capacitive element 55, and the charge amount accumulated by the photodiode 53 is read out by the amplifier 54 as a potential signal. The potential signal is A/D-converted to detect the incoming radiation dose.

Figure 13:
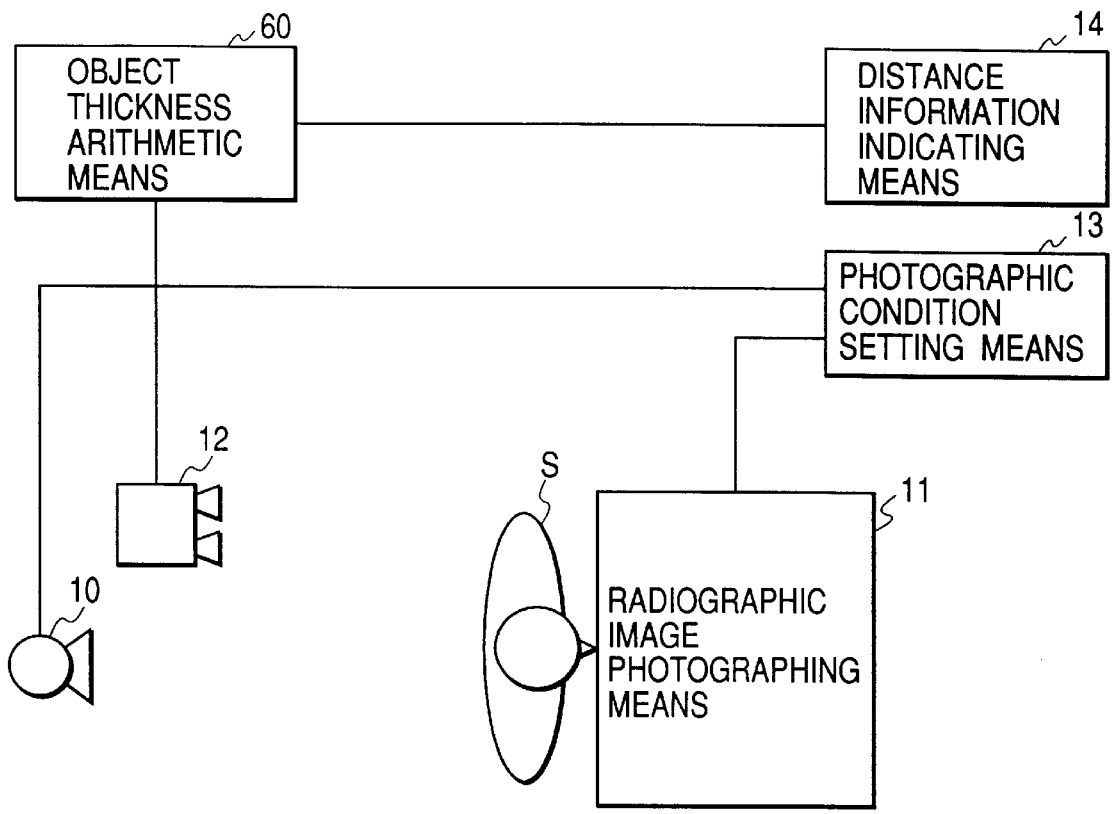
FIG. 13 is a diagram showing the arrangement according to the second embodiment of the present invention.

FIG. 13 is a diagram showing the arrangement of a radiographic apparatus according to the second embodiment of the present invention. An object thickness arithmetic means 60 is connected between the automatic distance measuring means 12 and distance information indicating means 14 shown in FIG. 7, and calculates the body thickness of the object S on the basis of the distances or distance from the radiation generating means 10 to the radiographic image photographing means 11 and/or object S. Other arrangements are the same as those in the first embodiment.

The body thickness of the object S is calculated from the difference between the relative distance between the radiographic image photographing means 11 and automatic distance measuring means 12, that is obtained by projecting a beam spot onto the front surface, e.g., the breast contact surface, of the radiographic image photographing means 11, and the relative distance between the object S and automatic distance measuring means 12, that is obtained by projecting a beam spot onto the object S. The distance information indicating means 14 indicates the distance information obtained by the automatic distance measuring means 12 and/or the object thickness information obtained by the object thickness arithmetic means 60.

Figure 14:
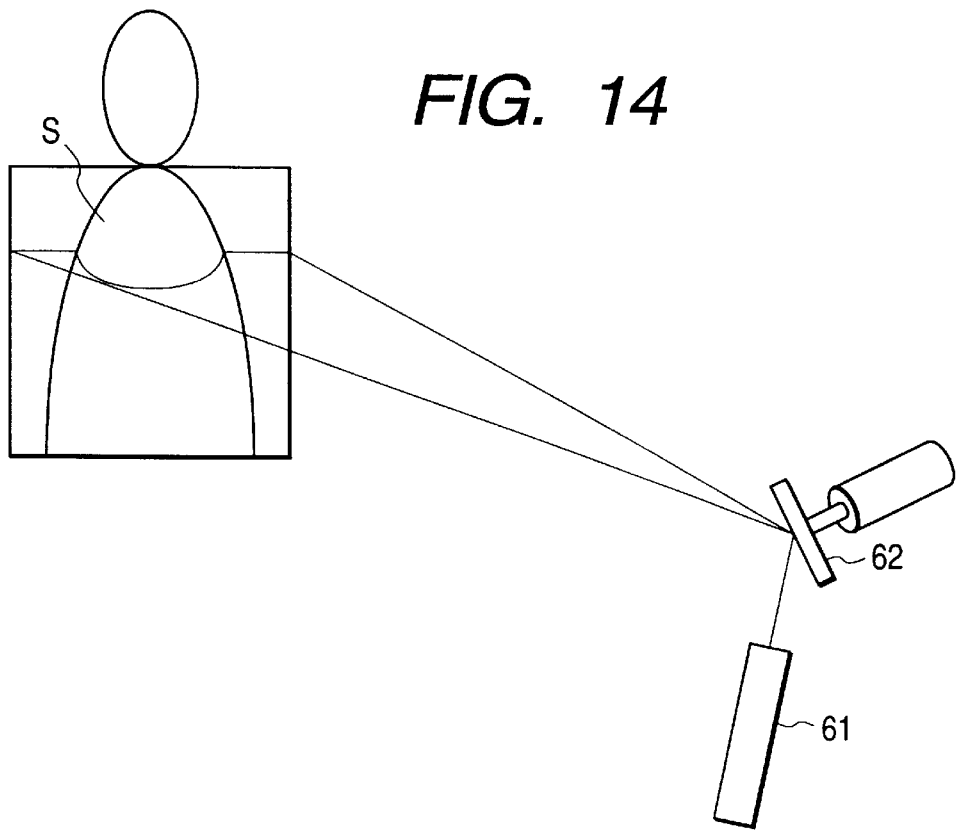
FIG. 14 is an explanatory view of body thickness measurement by means of a rotary mirror.
Figure 15:
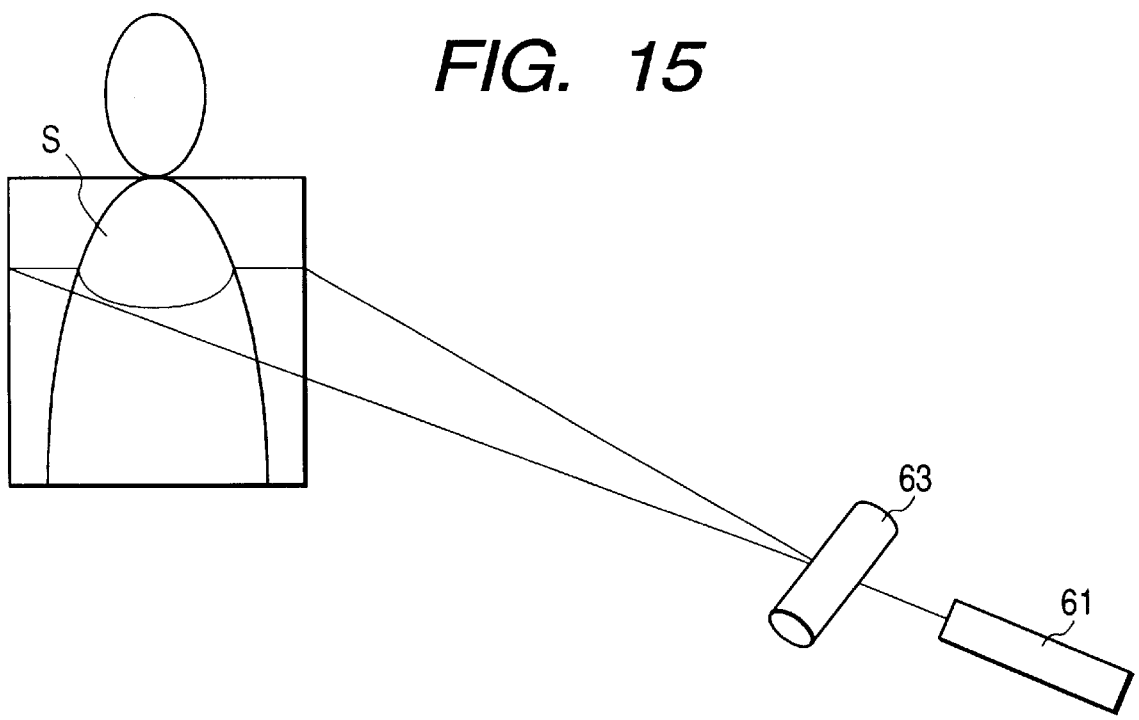
FIG. 15 is an explanatory view of body thickness measurement by means of a cylindrical lens.
Figure 16:
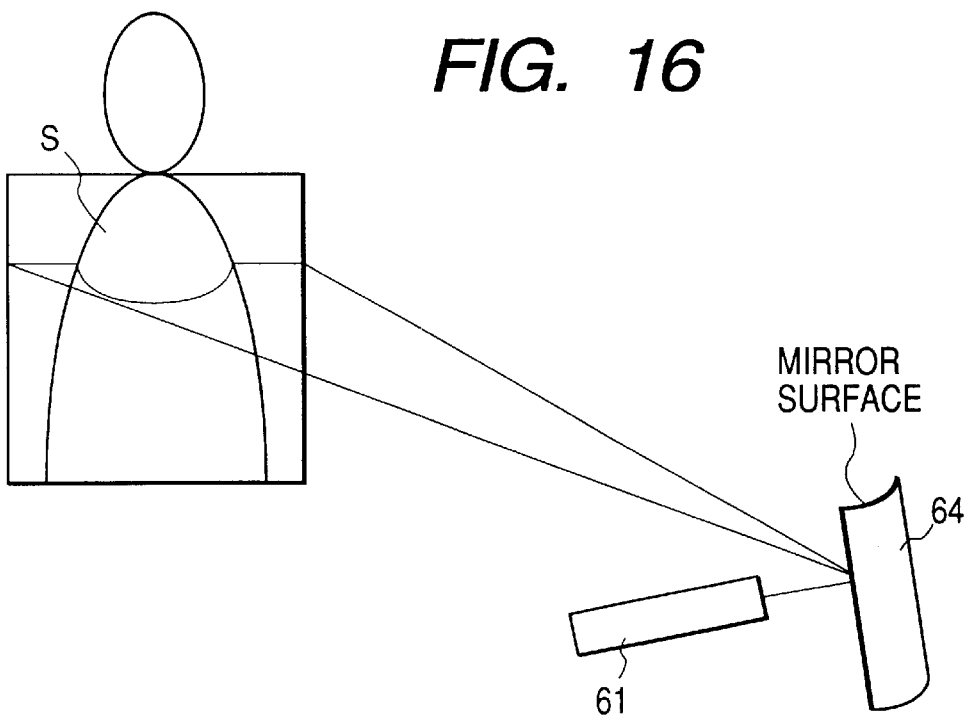
FIG. 16 is an explanatory view of body thickness measurement by means of a cylindrical mirror.

In the above-mentioned embodiment, a beam spot is projected onto the object S, and the distance to that point is calculated. Alternatively, as shown in FIG. 14, a laser beam emitted by a light source 61 may be scanned as a beam spot on the object S using a rotary mirror 62, so that the body thickness of a light sectional plane of the object S can be measured. Also, as shown in FIG. 15, a laser beam emitted by the light source 61 may be expanded to a single band using a cylindrical lens 63, and be projected onto the object S, so that the body thickness of the light sectional plane of the object S can be measured. Similarly, as shown in FIG. 16, a laser beam emitted by the light source 61 may be reflected by a cylindrical mirror 64 to measure the body thickness of the light sectional plane of the object.

Figure 17:
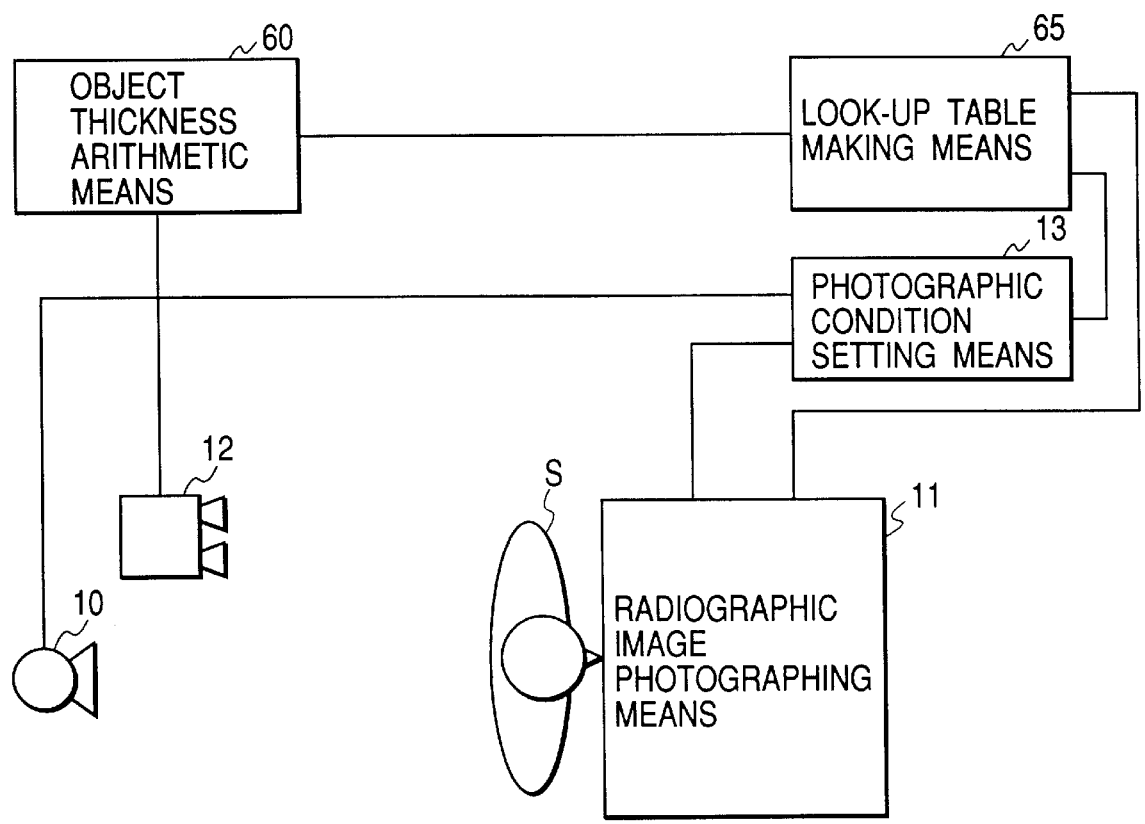
FIG. 17 is a diagram showing the arrangement according to the third embodiment of the present invention.

FIG. 17 is a diagram showing the arrangement of a radiographic apparatus according to the third embodiment. The radiographic image photographing means 11, the photographing condition setting means 13 represented by, e.g., a keyboard, and the automatic distance measuring means 12 are connected to a look-up table making means 65, which makes a look-up table using one or both data. In the following description, a detailed description of the same portions as those in the first and second embodiments will be omitted.

Figure 18:
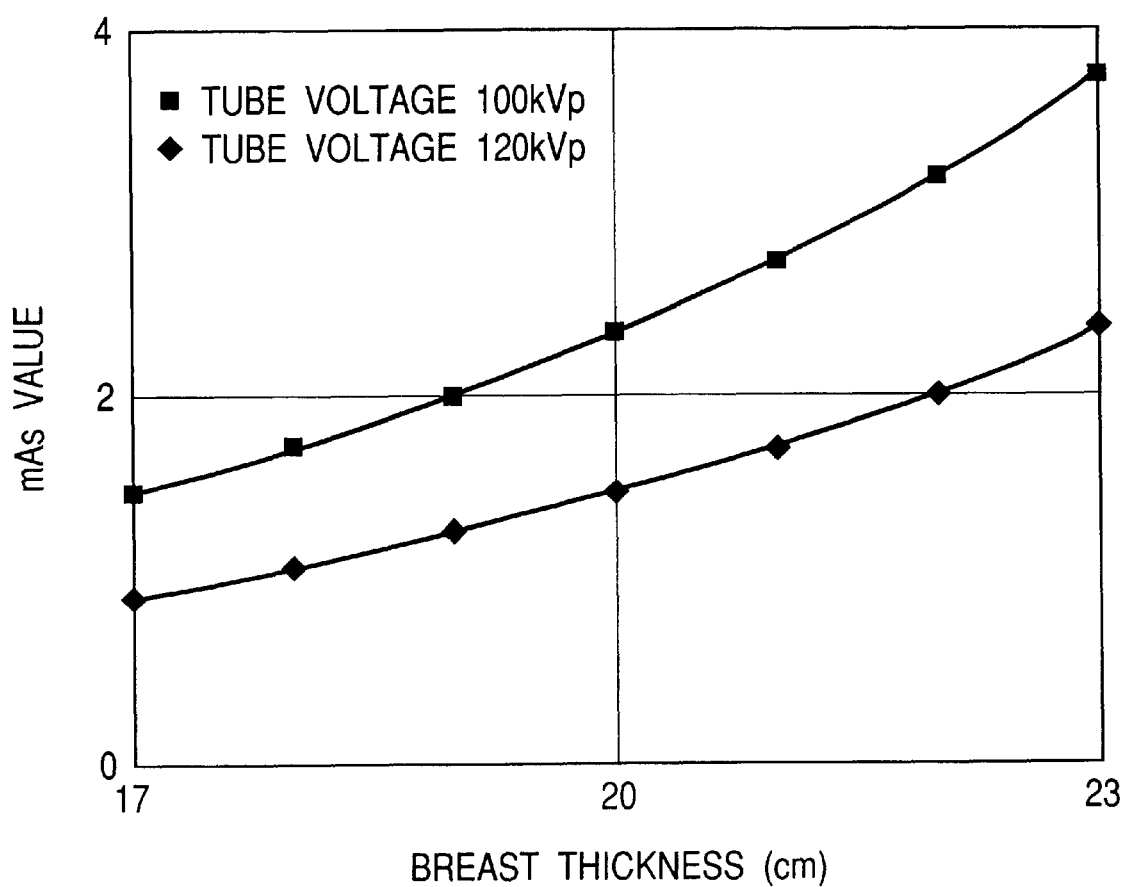
FIG. 18 is a graph showing the relationship between the breast thickness and mAs value.

FIG. 18 is a graph serving as a look-up table, which shows the relationship between the mAs value (tube current× irradiation time) and the breast thickness of a patient as the object S. FIG. 18 plots the mAs value versus breast thickness for tube voltages of 100 and 120 kVp when the intensity information or radiographic image information of radiation transmitted through patients respectively having breast thicknesses of 17, 18, 19, 20, 21, 22, and 23 cm outputs a constant value, and approximates the plotted values by an exponential function or quadratic function.

FIG. 18 exemplifies the relationship between the mAs value and breast thickness for seven patients with different breast thicknesses. Alternatively, when the relationship between the mAs value and breast thickness is obtained and averaged for a larger number of patients, a look-up table can be made more accurately. Also, the look-up table may be made using a phantom consisting of a substance having a transmittance equivalent to that of human body without using actual patient data.

The look-up table can also hold, as information, all or some of the following photographing conditions such as the photographing distance, photographing portion, photographing posture, thickness of the object S, type of intensifying paper, type of film, type of scattered radiation removal filter, type of additional filter, and the like, in addition to the tube voltage, breast thickness, and mAs value. For example, an approximation function formula representing the relationship between the breast thickness and mAs value for each tube voltage, and all or some of numerical values obtained by such approximation function formula may be held in a memory or a recording medium such as an HDD.

Figure 19:
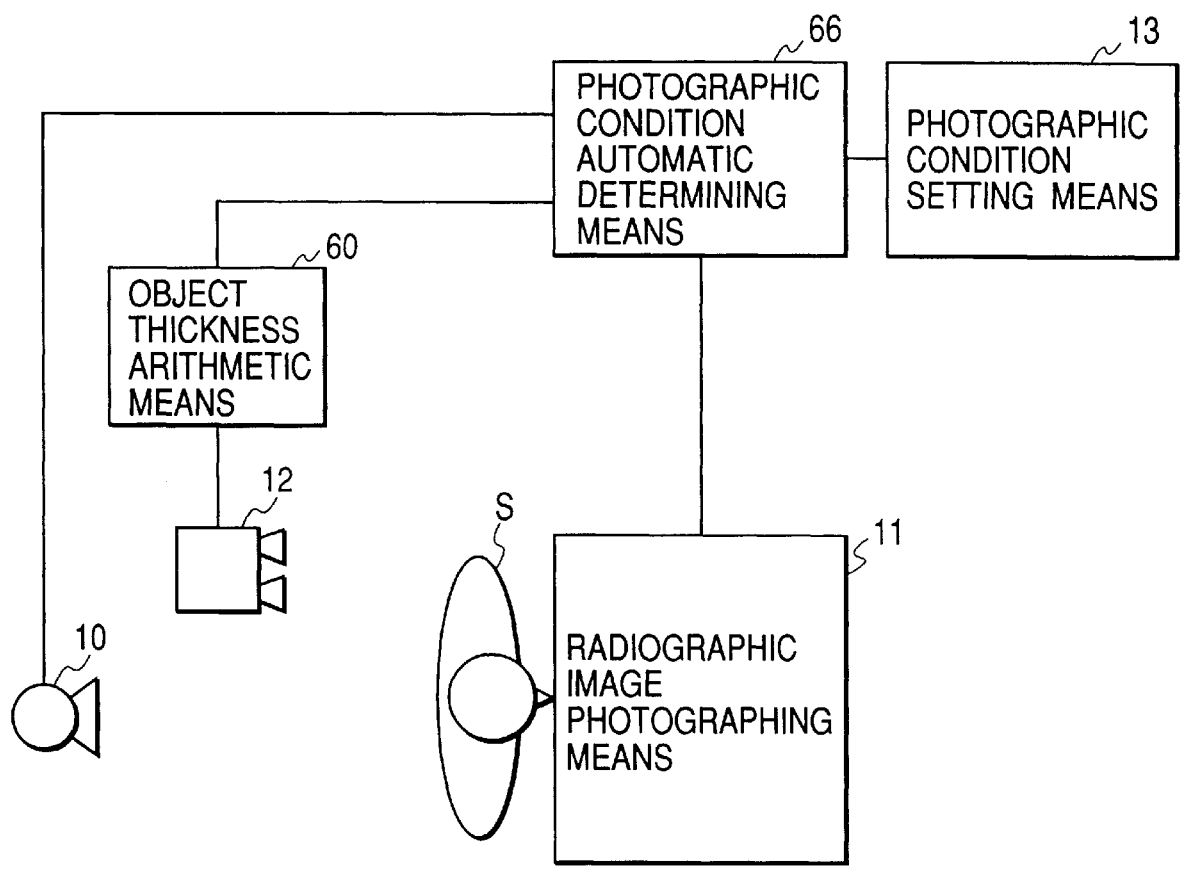
FIG. 19 is a diagram showing the arrangement according to the fourth embodiment of the present invention.

FIG. 19 is a diagram showing the arrangement of a radiographic apparatus according to the fourth embodiment. A photographing condition automatic determining means 66 is connected to the radiation means 10, radiographic image photographing means 11, photographing condition setting means 13, and object thickness arithmetic means 60. In the following description, a detailed description of the same portions as those in the first to third embodiments will be omitted.

When the photographing condition automatic determining means 66 determines the photographing conditions using the look-up table shown in, e.g., FIG. 18, in an irradiation time determining mode in which the operator sets the tube voltage and tube current using the photographing condition setting means 13, and the photographing condition automatic determining means 66 determines the irradiation time, if, for example, the tube current and tube voltage are respectively set at A (mA) and 100 (kVp) by the photographing condition setting means 13, and the object thickness arithmetic means 60 measures 21.5 (cm) as the breast thickness of a patient, the mAs value need only be set at 2.9 with reference to the look-up table, and an irradiation time T (sec) can be determined by 2.9/T.

On the other hand, in a tube current determining mode in which the operator sets the tube voltage and irradiation time at the photographing condition setting means 13 and the photographing condition automatic determining means 66 determines the tube current, if, for example, the irradiation time and tube voltage are respectively set at T (sec) and 100 (kVp) by the photographing condition setting means 13, and the object thickness arithmetic means 60 measures 21.5 (cm) as the breast thickness of a patient, the tube current (mA) can be determined by 2.9/T.

Furthermore, in a tube voltage determining mode in which the operator sets the tube current and irradiation time at the photographing condition setting means 13 and the photographing condition automatic determining means 66 determines the tube voltage, if, for example, the tube current and irradiation time are respectively set at 40 (mA) and 0.05 (sec) by the photographing condition setting means 13, i.e., the mAs value is 2, and the object thickness arithmetic means 60 measures 21.5 (cm) as the breast thickness of a patient, the tube voltage can be determined to be 100+{α/

$(\alpha+\beta)\} \times (120-100)$ (kVp) from the ratio $\alpha:\beta$ at intersections c of 2 mAs and the breast thickness of 21.5 (cm) for 100 (kVp) and 120 (kvP), with reference to the look-up table. When a look-up table holds information for more tube voltages, e.g., those in 5 (kVp) increments, the tube voltage can be determined more accurately.

Figure 20:
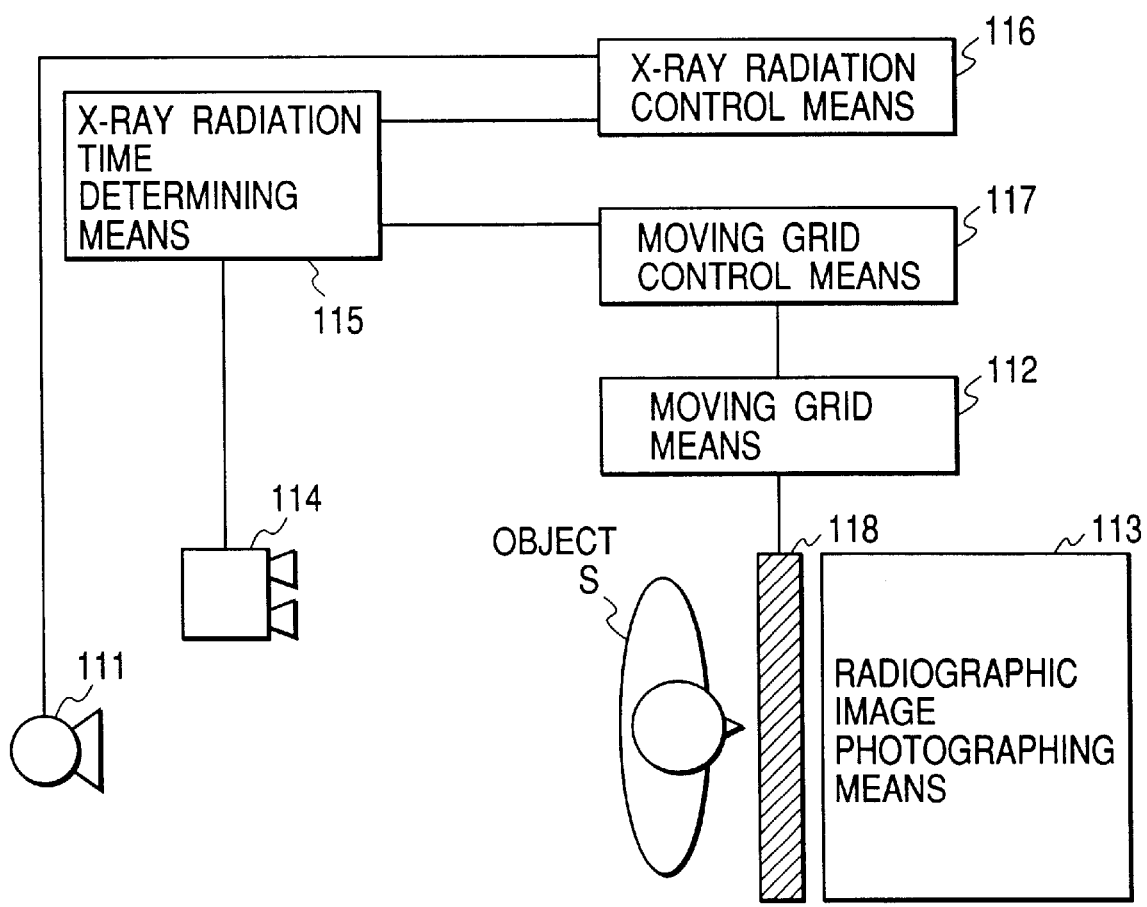
FIG. 20 is a diagram of an X-ray photographing apparatus according to the fifth embodiment of the present invention.

FIG. 20 is a diagram showing an X-ray photographing apparatus according to the fifth embodiment of the present invention. As shown in FIG. 20, the apparatus comprises an X-ray irradiation means 111 for generating X-rays, a grid 118 which is arranged in front of the irradiation means 111 and removes scattered X-rays, a moving grid means 112 for translating the grid 118, and an X-ray photographing means 113 for photographing an X-ray image transmitted through the grid 118. The X-ray photographing means 113 is a device using, e.g., a screen film, photostimulable phosphor, solid-state imaging element, or the like as an X-ray image receiving surface.

An object thickness measuring means 114 for measuring the body thickness of the object S, and an X-ray radiation or irradiation time determining means 115 for determining the X-ray irradiation time on the basis of the object thickness information obtained by the object thickness measuring means 114 are connected to an X-ray radiation or irradiation control means 116 and a moving grid control means 117. The X-ray irradiation control means 116 controls the X-ray irradiation means 111 on the basis of the X-ray irradiation time. Also, the moving grid control means 117 controls the moving grid means 112 on the basis of the determined X-ray irradiation time.

Figure 21:
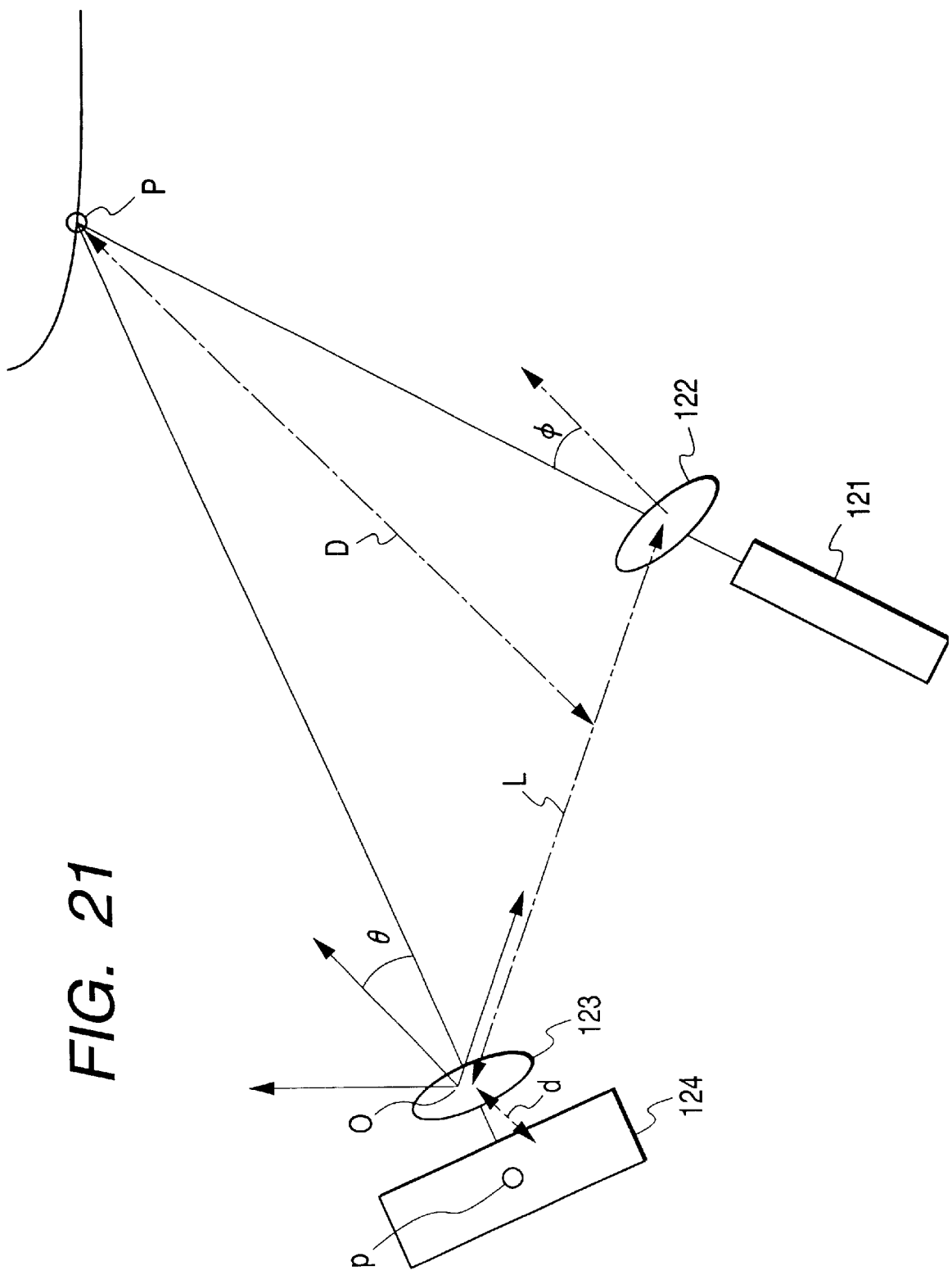
FIG. 21 is an explanatory view of the principle of body thickness measurement.

FIG. 21 shows the principle of thickness measurement by the object thickness measuring means 114. A light beam emitted by a light source 121, e.g., a laser diode is focused by a projection optical system 122, and forms a small beam spot P on the observation surface. This beam spot P is imaged on a position detection element 124, e.g., a CCD sensor, by an imaging optical system 123, and forms a beam spot image p. A relative distance Z between the beam spot P on the observation surface and the object thickness measuring means 114 can be calculated from the coordinate position of the beam spot image p on the position detection element 124.

Assume that the principal point of the imaging optical system 123 defines an origin O, the imaging plane of the position detection element 124 is set at a position of Z=−d, and the principal point of the projection optical system 122 is set at a position of X=L. When the beam spot P formed on the observation surface by a light beam irradiated in a $\phi$ direction with respect to the origin O is observed from the origin O in a $\theta$ direction, a relative distance D to the beam spot P is given by:

$$D = L/(\tan \theta + \tan \phi)$$

The angle $\theta$ is given by:

$$\theta = \tan^{-1}(x/d)$$

where x is the x-coordinate of the beam spot image p on the position detection element 124.

The body thickness of the object can be calculated from the difference between the relative distance between the X-ray photographing means 113 and object thickness measuring means 114, that is obtained by projecting a beam spot onto, e.g., the X-ray photographing means 113, and the relative distance between the object S and object thickness measuring means 114, that is obtained by projecting a beam spot onto the object S.

Figure 22:
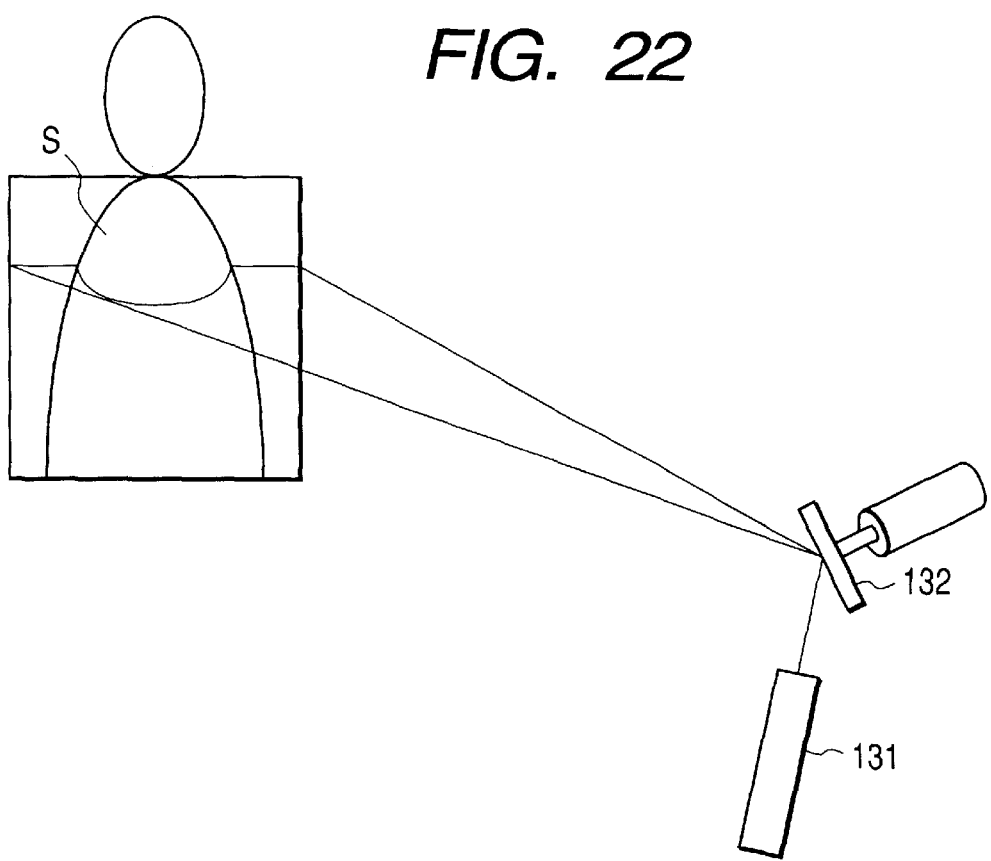
FIG. 22 is an explanatory view of an example using a rotary mirror.

In the above-mentioned method, a beam spot is projected onto the object, and the distance to that point is calculated. Alternatively, as shown in FIG. 22, a laser beam emitted by a light source 131 may be scanned as a beam spot on the object using a rotary mirror 132, so that the body thickness of a light sectional plane of the object can be measured.

Figure 23:
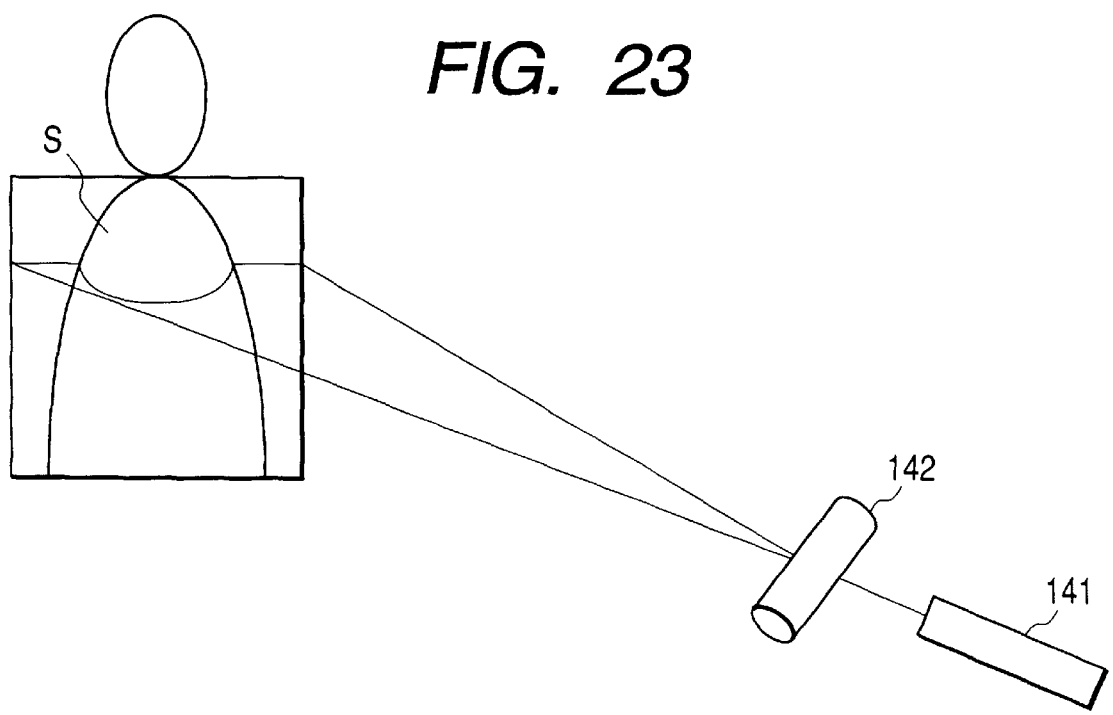
FIG. 23 is an explanatory view of an example using a cylindrical lens.

Also, as shown in FIG. 23, a laser beam emitted by a light source 141 may be expanded to a single band using a cylindrical lens 142, and be projected onto the object, so that the body thickness of the light sectional plane of the object can be measured.

Figure 24:
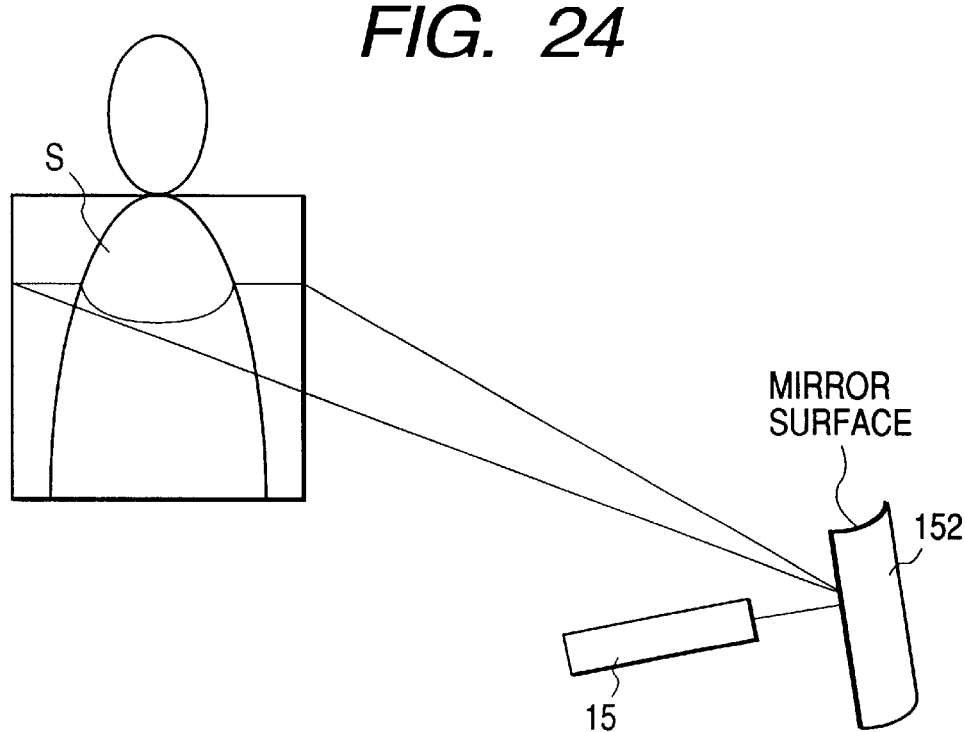
FIG. 24 is an explanatory view of an example using a cylindrical mirror.

Furthermore, as shown in FIG. 24, a laser beam emitted by a light source 151 may be reflected by a cylindrical mirror 152 to measure the body thickness of the light sectional plane of the object.

Figure 25:
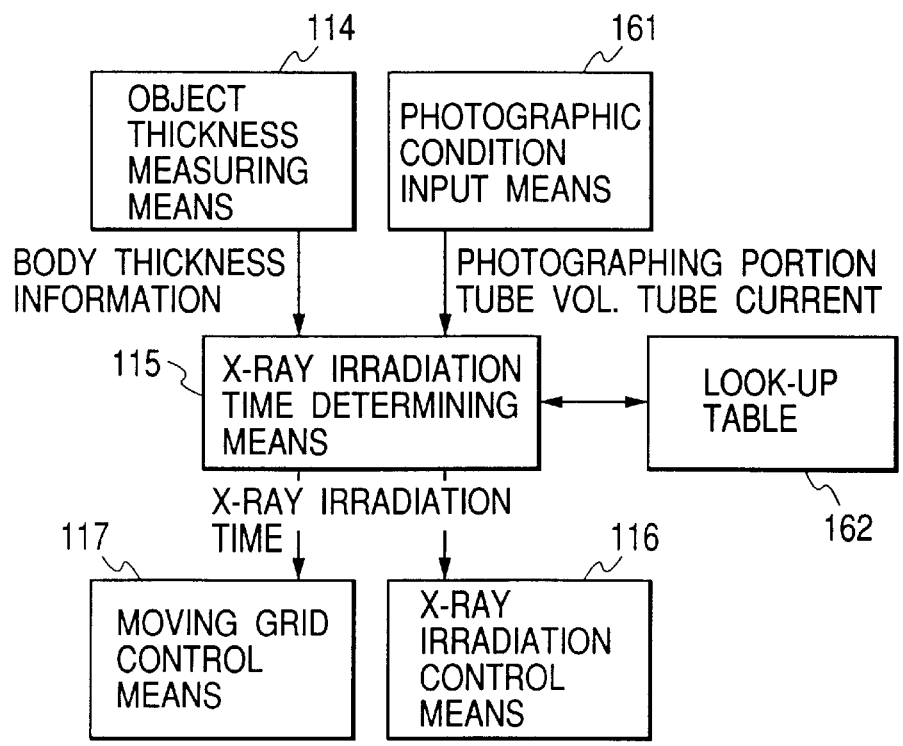
FIG. 25 is a diagram showing the arrangement of an X-ray irradiation time determining means.

FIG. 25 shows an example of the diagram of the X-ray irradiation time determining means. The body thickness information measured by the object thickness measuring means 114, and photographing condition information such as a photographing portion, tube voltage, tube current, and the like, input at a photographing condition input means 161 such as a control panel, are input to the X-ray irradiation time determining means 115. The X-ray irradiation time determining means 115 determines the X-ray irradiation time with reference to a look-up table 162 that holds the irradiation conditions with respect to the body thickness of the object at each tube voltage, and outputs the X-ray irradiation time information to the X-ray irradiation control means 116 and the moving grid control means 117.

Figure 26:
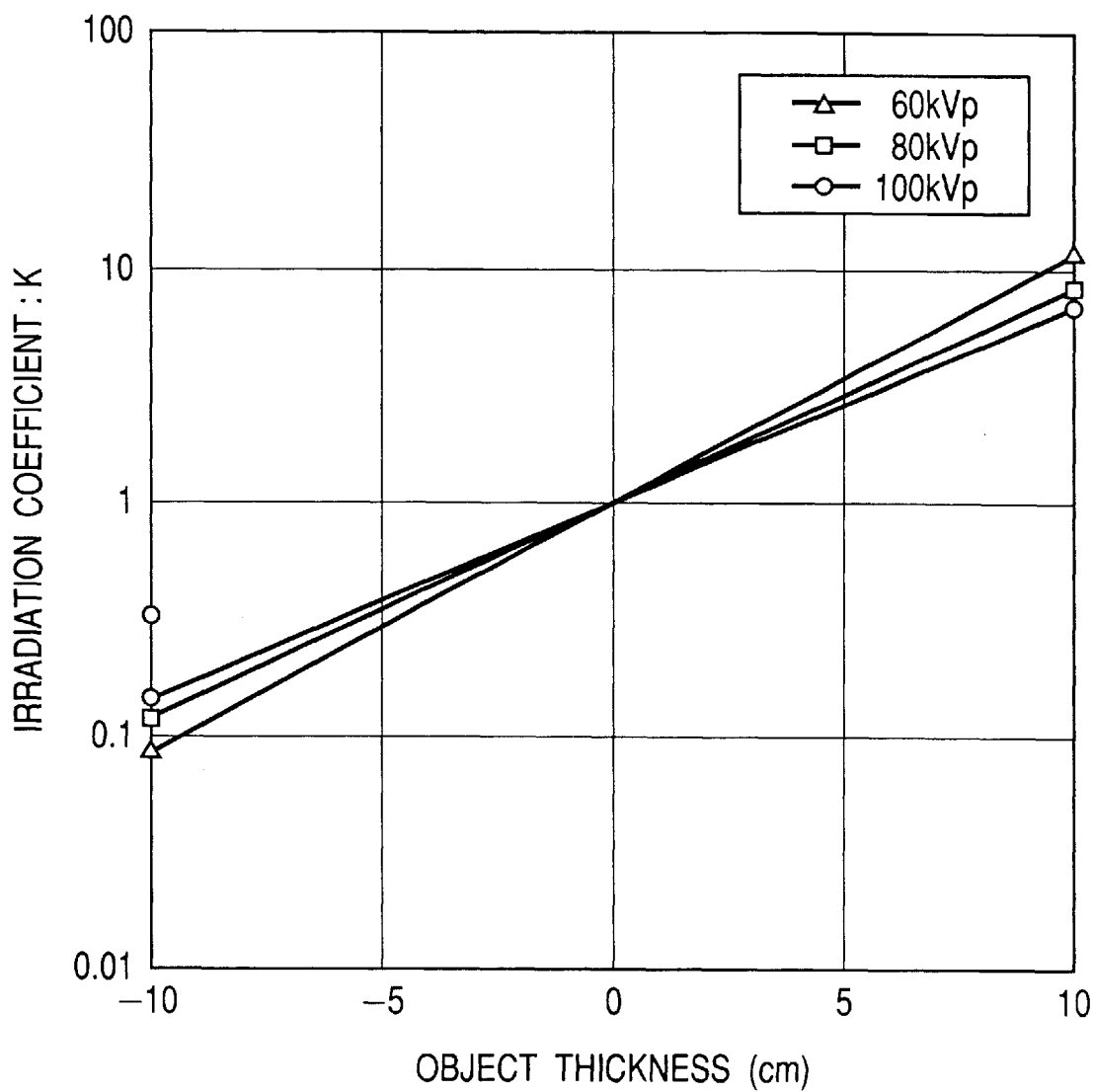
FIG. 26 is a graph showing the irradiation coefficient as a function of object thickness.

FIG. 26 is a graph showing an example of the look-up table 162 that shows an irradiation coefficient K as a function of object thickness. If $d_1$ is the reference body thickness, $I_1$ the dose to be irradiated, $d_2$ the body thickness of the object to be photographed, $I_2$ the dose to be irradiated onto the object to obtain an identical density, then the irradiation coefficient K is given by:

$$K = I_2/I_1 = Ie^{\mu d_2}/Ie^{\mu d_1} = e^{\mu(d_2-d_1)}$$

where I is the dose transmitted through the object, $\mu$ the attenuation factor of the object, and e the base of the natural logarithm.

That is, in order to obtain a reference density in objects with different body thicknesses $d_2$, a dose corresponding to a multiple of the following value is required:

$$e^{\mu(d_2-d_1)}$$

In this manner, the X-ray irradiation time determining means 151 obtains a value $I_1 \times K$ with reference to the look-up table 162 on the basis of the tube current information A and tube voltage information input at the photographing condition input means 161, and can determine the X-ray irradiation time T by:

$$T = I_1 \times K/A$$

Figure 27:
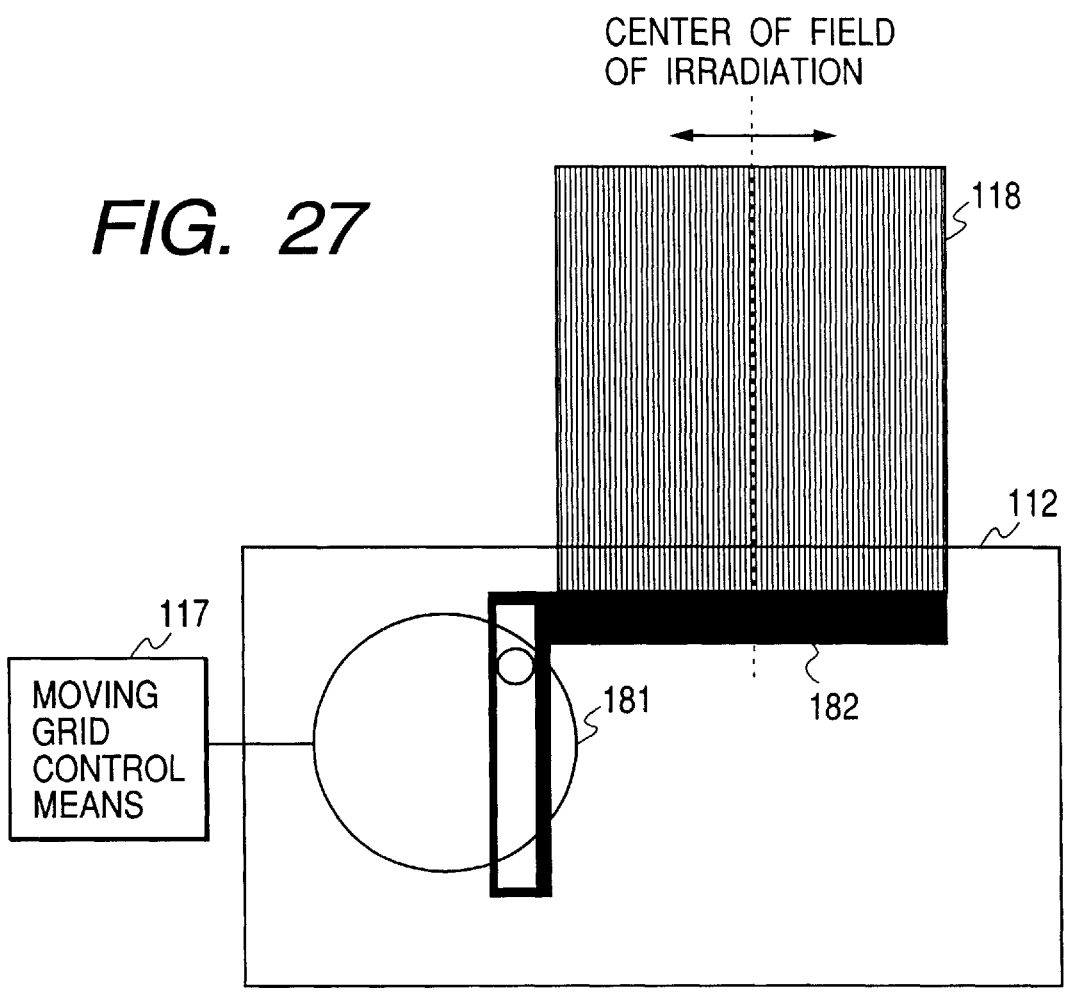
FIG. 27 is an explanatory view of a moving grid and its control means.

FIG. 27 shows an example of the arrangement of the grid 118, moving grid means 112, and moving grid control means 117. The moving grid means 112 comprises, e.g., a rotary motor 181, and a plate cam 182 for converting rotation of the rotary motor 181 into reciprocal motion. When a convergence grid having a convergence distance of f cm and a grid ratio r:1 is moved horizontally by b cm, the primary X-ray loss (%) is given by:

$$L = r \times b/f \times 100 \ (\%)$$

For example, when photographing is done using a grid having a convergence distance of 180 cm and a grid ratio 12:1, if the primary X-ray loss is to be reduced to 10% or less, the horizontal movement must be suppressed to 1.5 cm or less from the above equation.

The grid is moved by the same width on both sides of the center of the field of irradiation of X-rays during X-ray irradiation so as to equalize cutoff on the X-ray image. The moving grid control means 117 controls the rotary motor 181 to move the grid by predetermined widths on both sides of the center of the field of irradiation of X-rays during X-ray irradiation.

Figure 28:
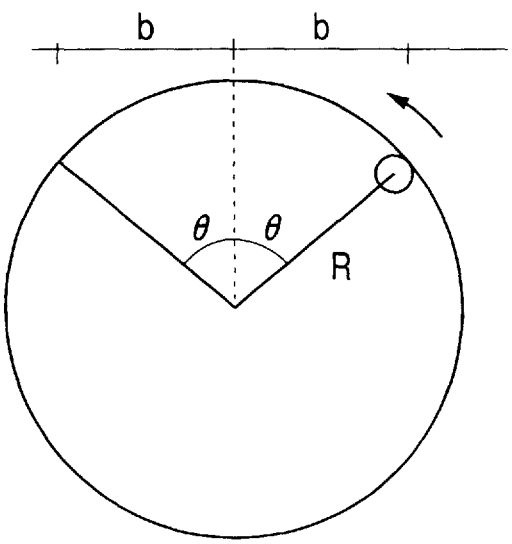
FIG. 28 is a view for explaining operation of the moving grid control means.

When the rotary motor 181 satisfies a given condition, the X-ray irradiation control means 116 controls to irradiate X-rays for the X-ray irradiation time determined by the X-ray irradiation time determining means 115. For example, as shown in FIG. 28, if the X-ray irradiation time determining means 115 determines the X-ray irradiation time=T, $2b$ represents the moving distance of the grid, and R the radius of rotation of the rotary motor 181, then the angle $2\theta$ of rotation of the rotary motor 181 during the X-ray irradiation time T is:

$$2\theta = \sin^{-1}(b/R) \times 2$$

Hence, the moving grid control means 117 controls the rotary motor 181 to rotate $2\theta$ during the X-ray irradiation time T.

The X-ray irradiation control means 116 controls to irradiate X-rays at a position where the contact point between the grid and plate cam 182 is $\theta$ before the center of the field of irradiation of X-rays, or at a position a delay time before $\theta$ in consideration of the system delay.

By minimizing the moving distance $2b$ of the grid during the X-ray irradiation time, for example, to 1 cm or less, the influence of grid cutoff can be removed.

As described above, according to this embodiment, since the body thickness of the object is measured before irradiation of radiation, the irradiation time is determined, and the moving grid is controlled on the basis of the irradiation time information, thus removing the influences of shadow images of lead foils formed in a radiographic image and providing a radiographic image which is easy to observe.

Figure 29:
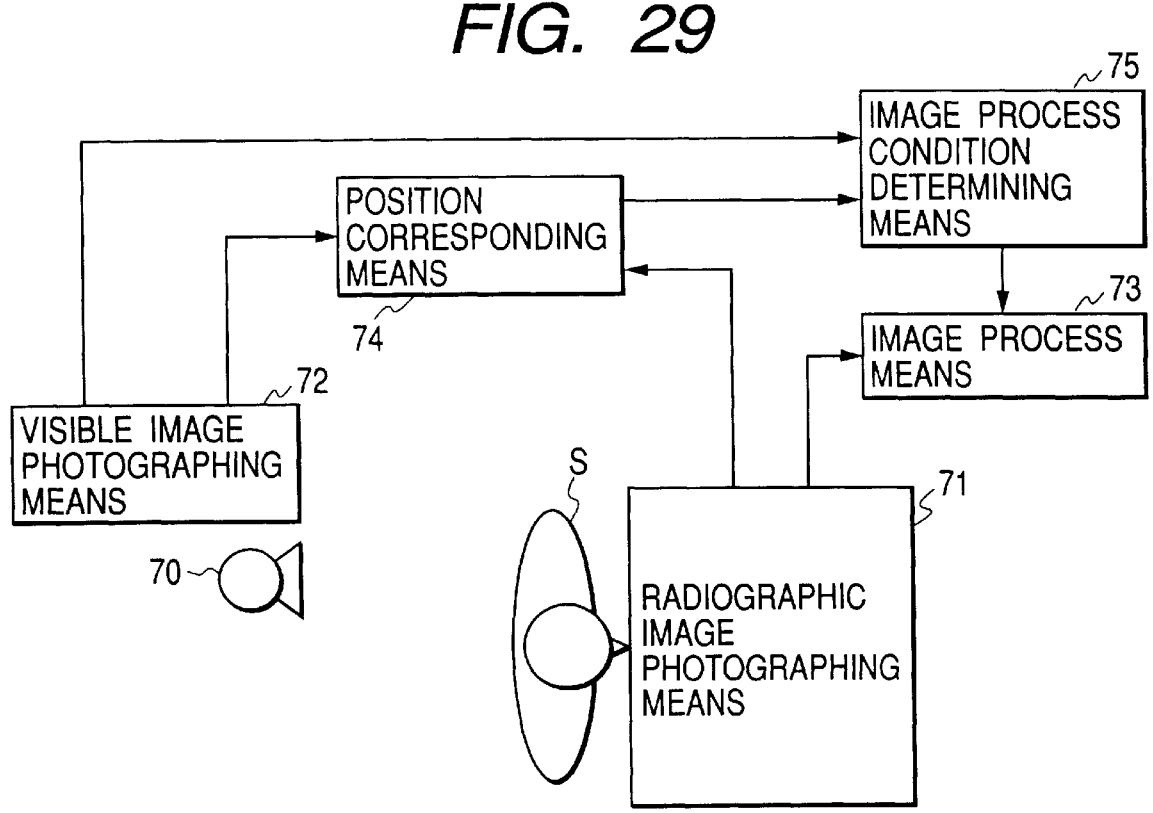
FIG. 29 is a diagram showing the arrangement according to the sixth embodiment of the present invention.

FIG. 29 is a diagram showing a radiographic apparatus according to the sixth embodiment. A radiographic image photographing means 71 is disposed in front of a radiation generating means 70 for generating radiation. The radiographic image photographing means 71 uses a photostimulable phosphor, photodetection array, or the like as an image receiving surface. A visible image photographing means 72 for photographing a visible image of an object S is disposed in the vicinity of the radiation generating means 70.

The output from the radiographic image photographing means 71 is connected to an image process means 73, which has image process functions of histogram analysis, gradation correction, frequency emphasis, and the like of image information obtained by the radiographic image photographing means 71. The output from the visible image photographing means 72 is connected to a position corresponding means 74, which also receives the output from the radiographic image photographing means 71. Furthermore, the output from the visible image photographing means 72 is connected to an image process condition determining means 75, the output of which is connected to the image process means 73. With this arrangement, the image process condition determining means 75 has a function of determining the image process conditions of the image process means 73 on the basis of visible image information obtained by the visible image photographing means 72.

Figure 30:
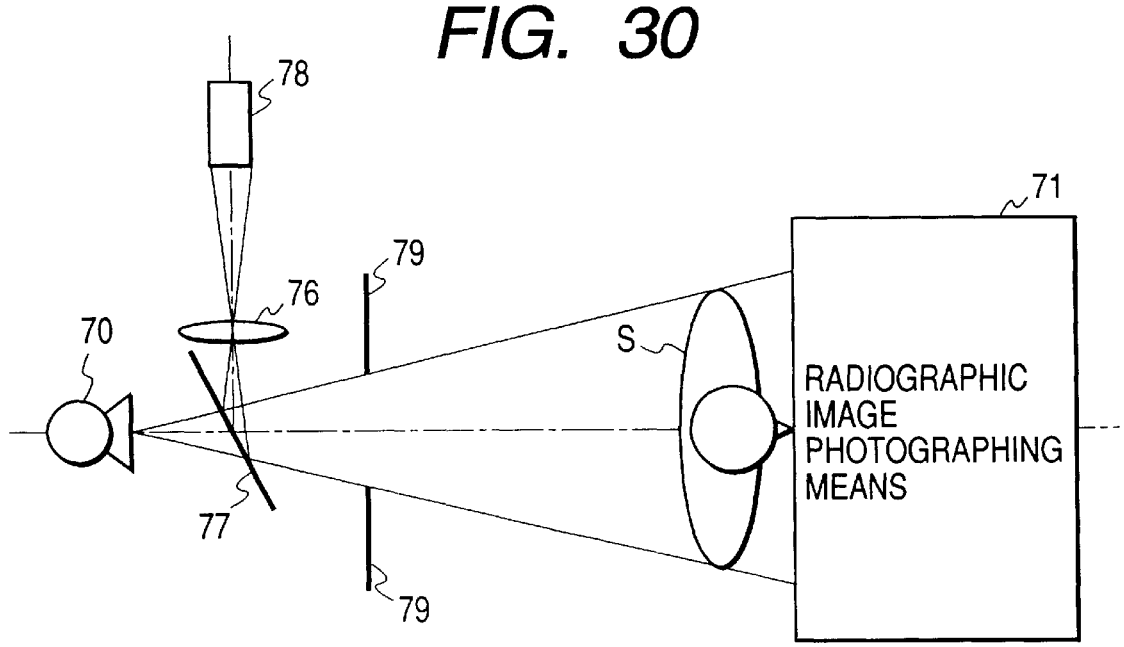
FIG. 30 is a view showing the arrangement of a visible image photographing means.

FIG. 30 shows the arrangement of the visible image photographing means 72. The visible image photographing means 72 comprises a return mirror 77 having high transmittance with respect to radiation, a CCD camera 78, and a movable aperture stop 79 for adjusting radiation to an arbitrary size. The CCD camera 78 has, e.g., 512×512 pixels and requires 8 bits for quantization, and can obtain a visible image that can be processed by black-and-white and versatile image process devices. Note that in FIG. 30 the optical axis of radiation agrees with that of the visible image photographing means 72, but they need not agree with each other as long as the positional relationship is appropriately calibrated.

Figure 31:
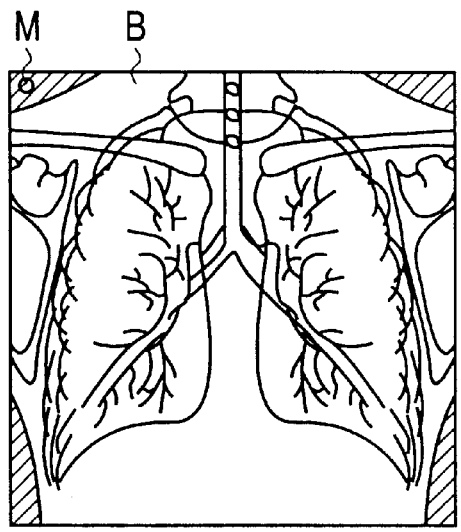
FIG. 31 is an explanatory view of a radiographic sensing region.
Figure 32:
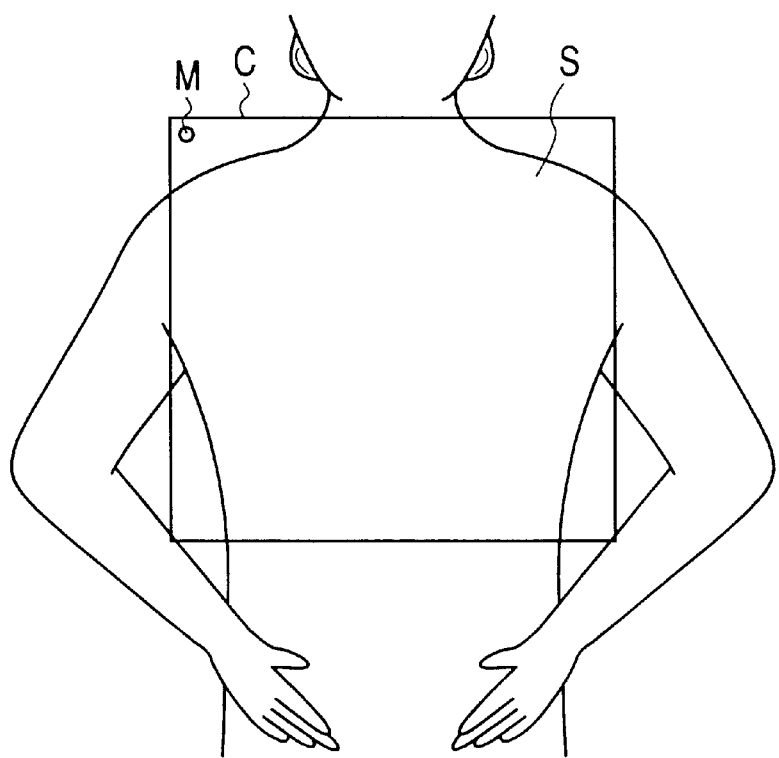
FIG. 32 is an explanatory view of a CCD camera sensing region.

With this arrangement, the radiation generating means 70 emits radiation toward the object S, and the radiation transmitted through the object S reaches the radiographic image photographing means 71, thus photographing a radiographic image. The radiographic image is subjected to image processes in the image process means 73 to obtain radiographic image information of the object S having a sensing region B, as shown in FIG. 31. On the other hand, the CCD camera 78 of the visible image photographing means 72 photographs a visible image of a sensing region C, as shown in FIG. 32.

For example, with reference to a mark M on the radiation incoming side of the radiographic image sensing means 71, the sensing region B of the radiographic image photographing means 71 is made to correspond to the sensing region C of the CCD 78, and the coordinate positions of visible image information obtained by the visible image photographing means 71 and image information obtained by the radiographic image photographing means 71 can be made to correspond to each other by the position corresponding means 74. Note that the visible information and radiographic information do not always have one-to-one correspondence therebetween. For example, if the visible information consists of 512×512 pixels, and radiographic information consists of 1024×1024 pixels, one pixel in the visible information corresponds to four pixels in the radiographic information. On the other hand, since the visible image information is imaged by a lens, the peripheral portion of the image may often be distorted. In such case, the distortion is preferably corrected before determining the correspondence with the radiographic information.

Figure 33:
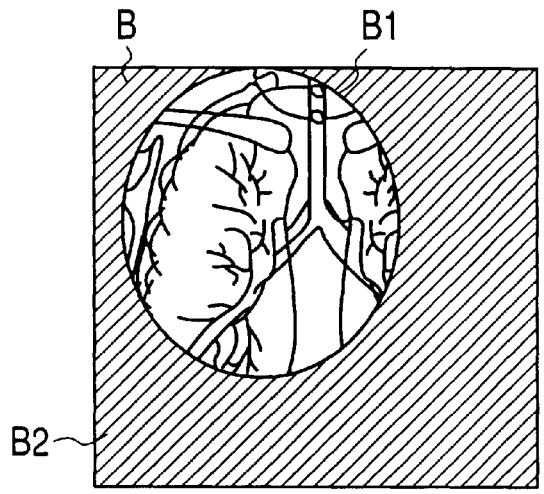
FIG. 33 is an explanatory view of a radiographic sensing region.
Figure 34:
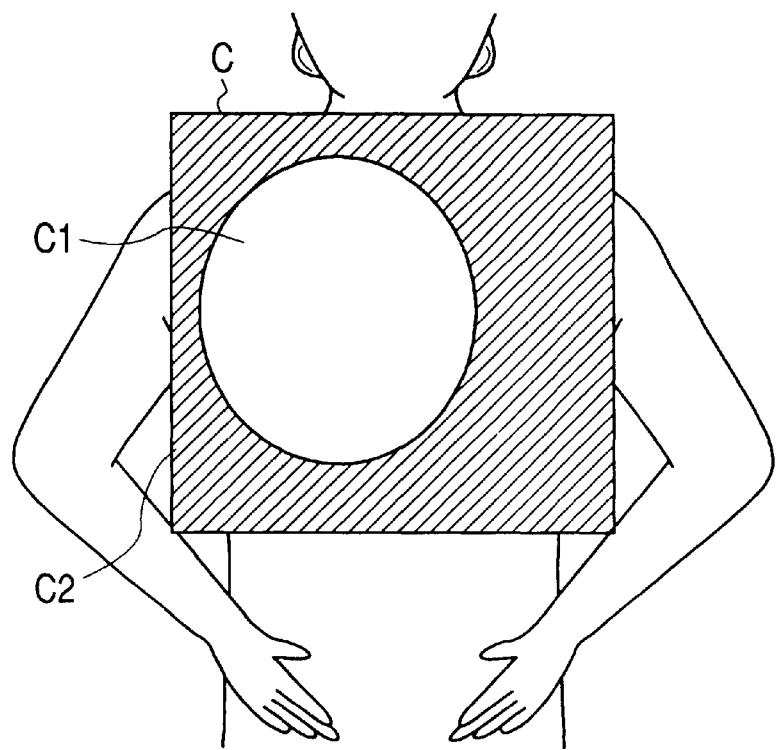
FIG. 34 is an explanatory view of a CCD camera sensing region.

When the image process condition determining means 75 comprises an irradiation field determining means for determining the field of irradiation, since the field of irradiation can be adjusted to an arbitrary size by the movable aperture stop 79 of the radiation generating means 70, the radiographic sensing region B is divided into an irradiated region B1 and a non-irradiated region B2 masked by the movable aperture stop 79, as shown in FIG. 33. Furthermore, as shown in FIG. 34, the visible image information photographed by the visible image photographing means 72 is divided into an irradiation field region C1 and a non-irradiation field region C2 by binarization, as shown in FIG. 34. Since these regions C1 and C2 can be made to correspond to the regions B1 and B2 of the radiographic image information by the position corresponding means 74, the image process means 73 performs image processes on the irradiation field region B1 of the radiographic image information.

Figure 35:
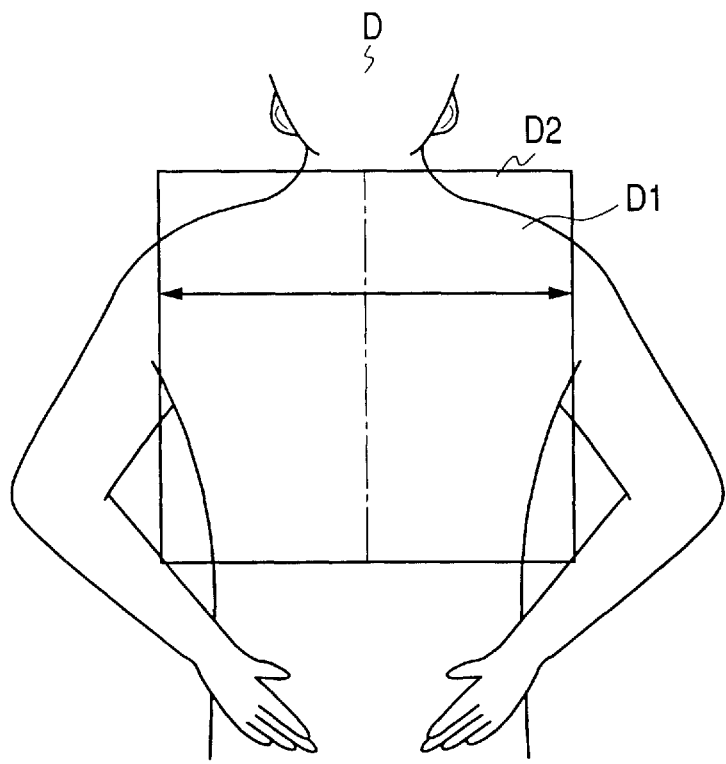
FIG. 35 is a front view of posture determination.
Figure 36:
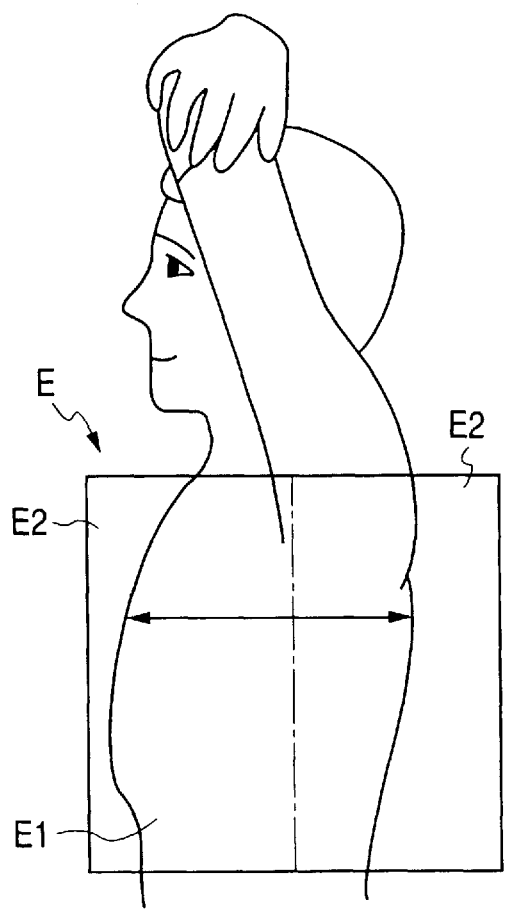
FIG. 36 is a side view of posture determination.

When the image process condition determining means 75 comprises a posture determining means for determining the postures of the object S in front and side shots, front and side shot images D and E of visible image information obtained by the visible image photographing means 72 are respectively divided into object regions D1 and E1, and non-object regions D2 and E2 by binarization, as shown in FIGS. 35 and 36. For example, whether a front or side shot D or E is to be obtained is determined on the basis of the widths (the lengths of double-headed arrows in FIGS. 35 and 36) of the object regions D1 and E1 and/or symmetry about the centers (one-dashed chain lines in FIGS. 35 and 36) of images and/or the presence/absence of the arms, and the like. Then, the determined posture information is supplied to the image process means 73, which executes image processes suitable for the object regions D1 and E1.

Figure 37:
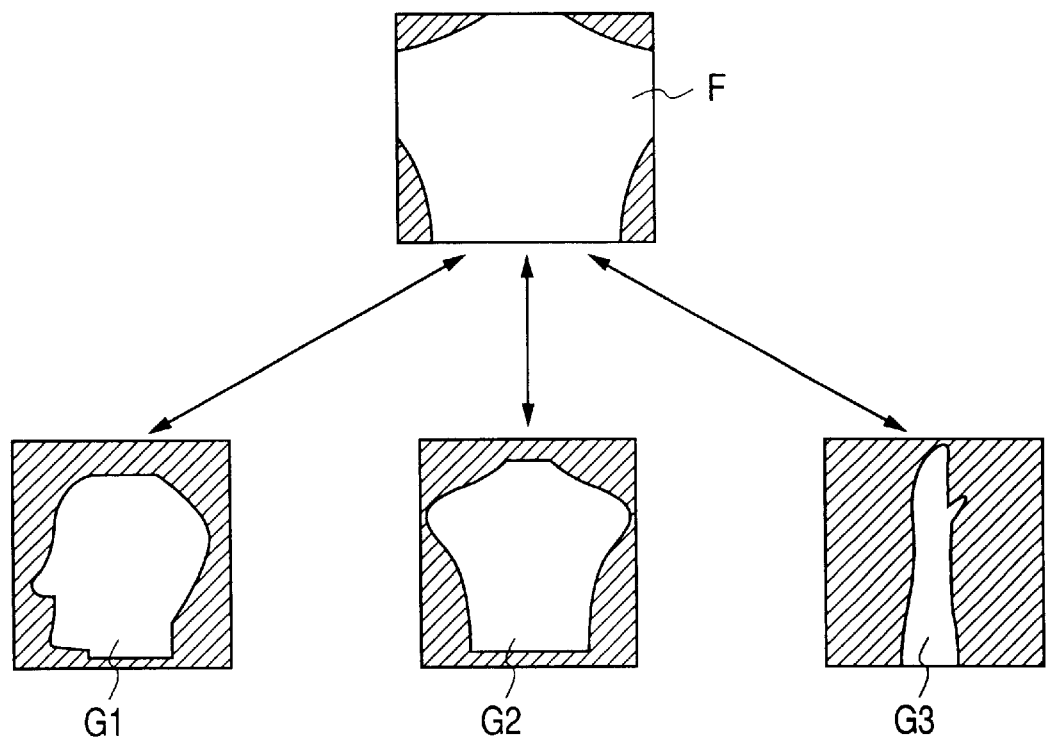
FIG. 37 is an explanatory view of portion determination.

Finally, when the image process condition determining means 75 comprises a photographing portion determining means for determining the photographing portion of the object S, a binary image F shown in FIG. 37 is generated by visible image information obtained by the visible image photographing means 72 by binarization. The binary image F is compared with a head template G1, breast template G2, and hand template G3. For example, errors between the binary image F and the individual portion templates G1, G2, and G3 are calculated in units of pixels, and the sum totals of errors are compared with a predetermined threshold value. When the sum total is smaller than the threshold value, the corresponding portion is determined to be the photographing portion. The portion information is then supplied to the image process means 73, which executes an image process suitable for the photographing portion in the object region of radiographic image information. Note that the head, breast, and hand alone have been described, but the abdomen, leg, and the like can be similarly determined.

Figure 1:
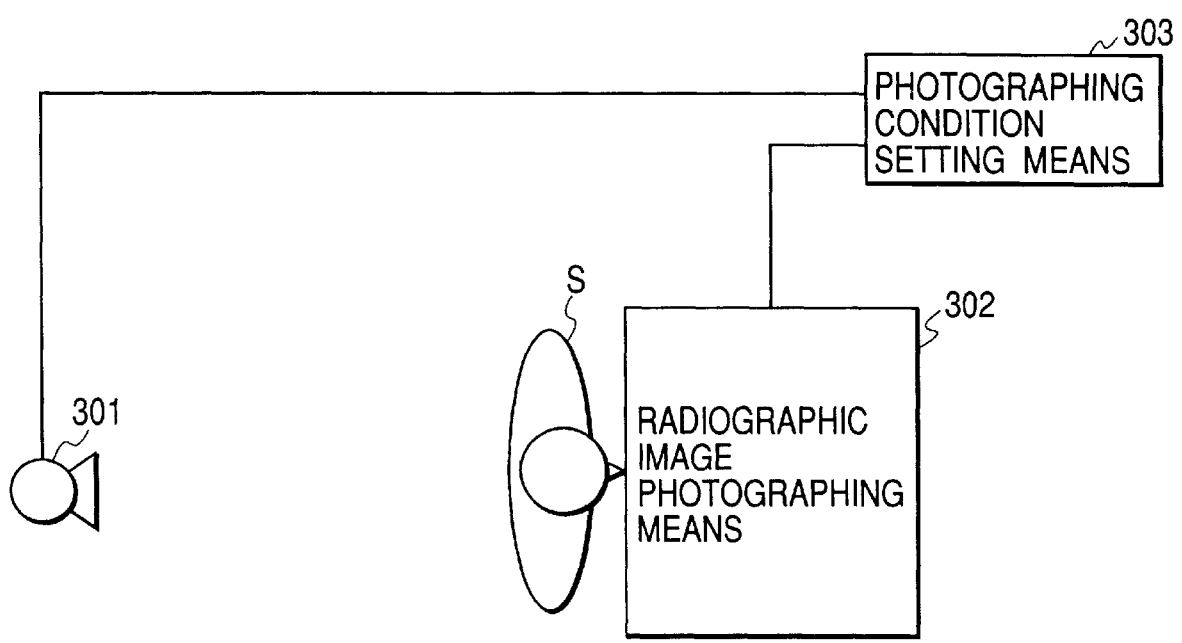
FIG. 1 is a diagram showing the arrangement of the first conventional art.
Figure 2:
FIG. 2 is an explanatory view of a parallel grid.
Figure 3:
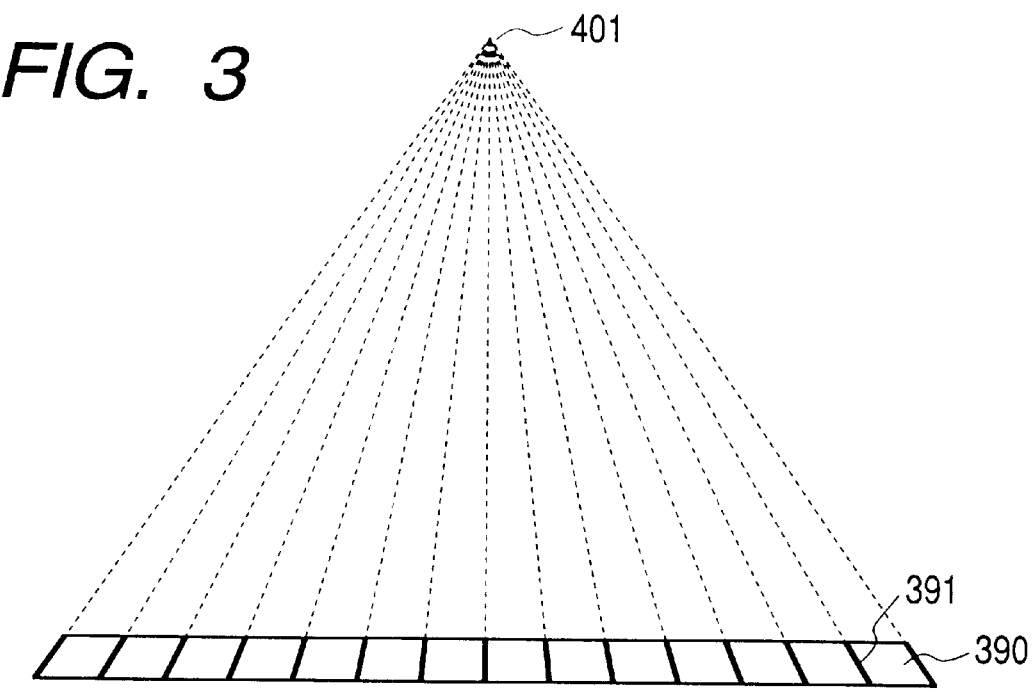
FIG. 3 is an explanatory view of a convergence grid.
Figure 4:
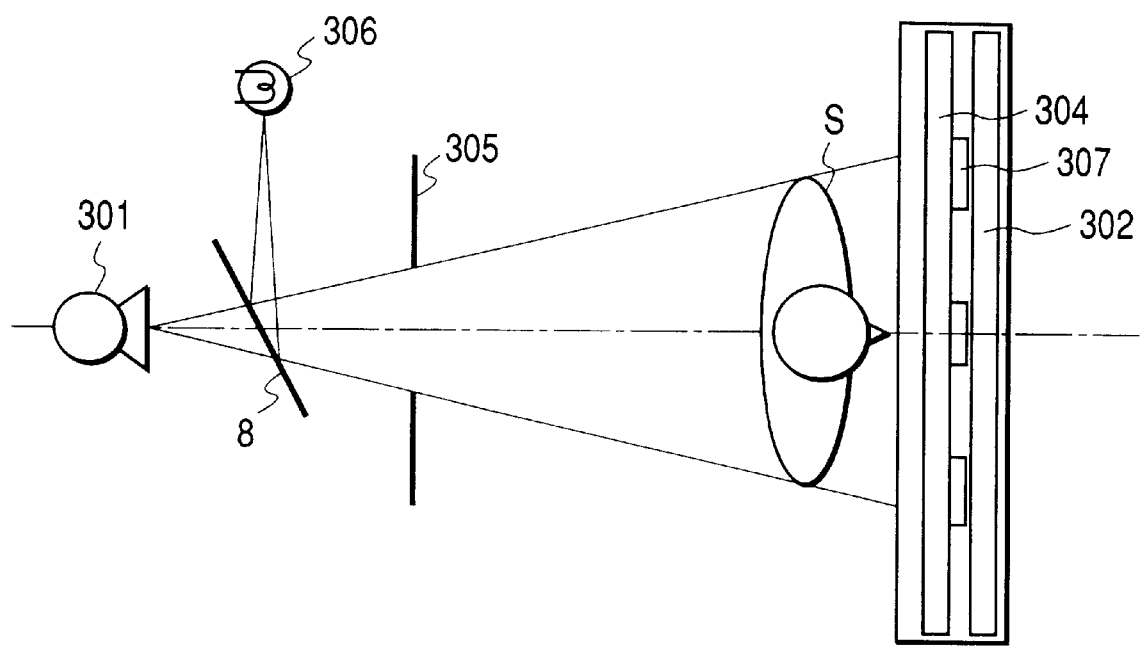
FIG. 4 is a view showing the arrangement of the third conventional art.
Figure 5:
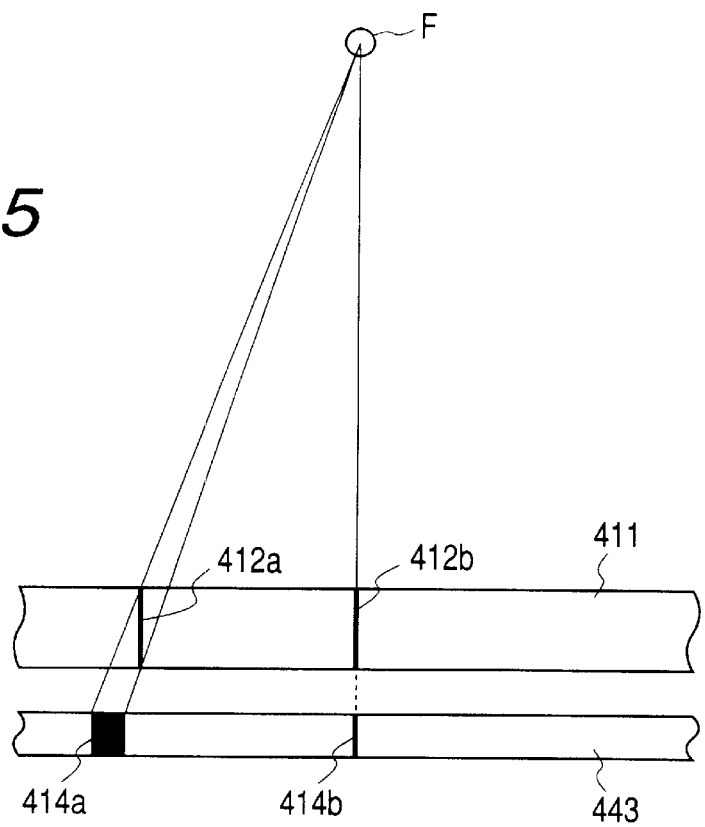
FIG. 5 is an explanatory view of cutoff of the parallel grid.
Figure 6:
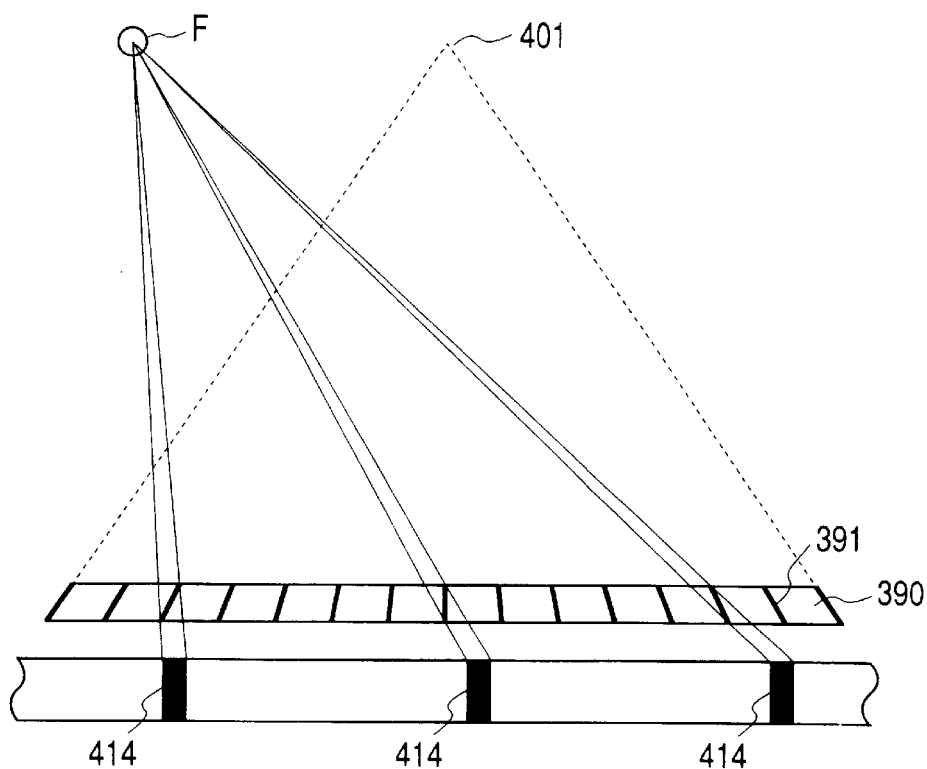
FIG. 6 is an explanatory view of horizontal deviation of the convergence grid.
Figure 38:
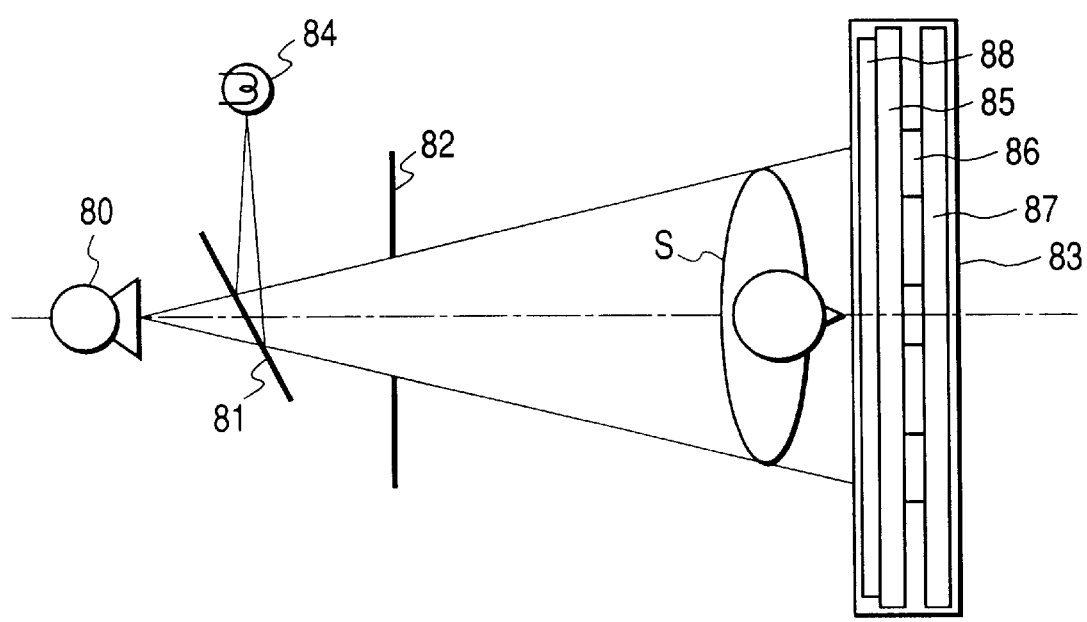
FIG. 38 is a view showing the arrangement according to the seventh embodiment of the present invention.

FIG. 38 shows the arrangement of a radiographic apparatus according to the seventh embodiment of the present invention. A return mirror 81, movable aperture stop 82, object S, and radiographic unit 83 are disposed in turn in front of a radiation generating means 80, and a light source 84 is disposed in the incident direction of the return mirror 81. The radiographic unit 83 comprises a grid 85, phototimer light-receiving unit 86, and radiographic image photographing means 87. The difference between this embodiment and the third embodiment shown in FIG. 4 is that an object information acquiring means 88 comprising a visible light sensor for obtaining two-dimensional information of the object S is disposed in front of the radiographic image photographing means 87.

In this manner, since the object information acquiring means 88 is arranged, one-to-one correspondence with the radiographic image photographing means 87 can be obtained. Hence, the radiographic image of the object S and two-dimensional information can be easily made to correspond to each other, and such system is particularly effective for a portable radiographic unit 83. Note that the wavelength range of light to be used in practice is not limited to visible light as long as it is not harmful to the human body.

Figure 39:
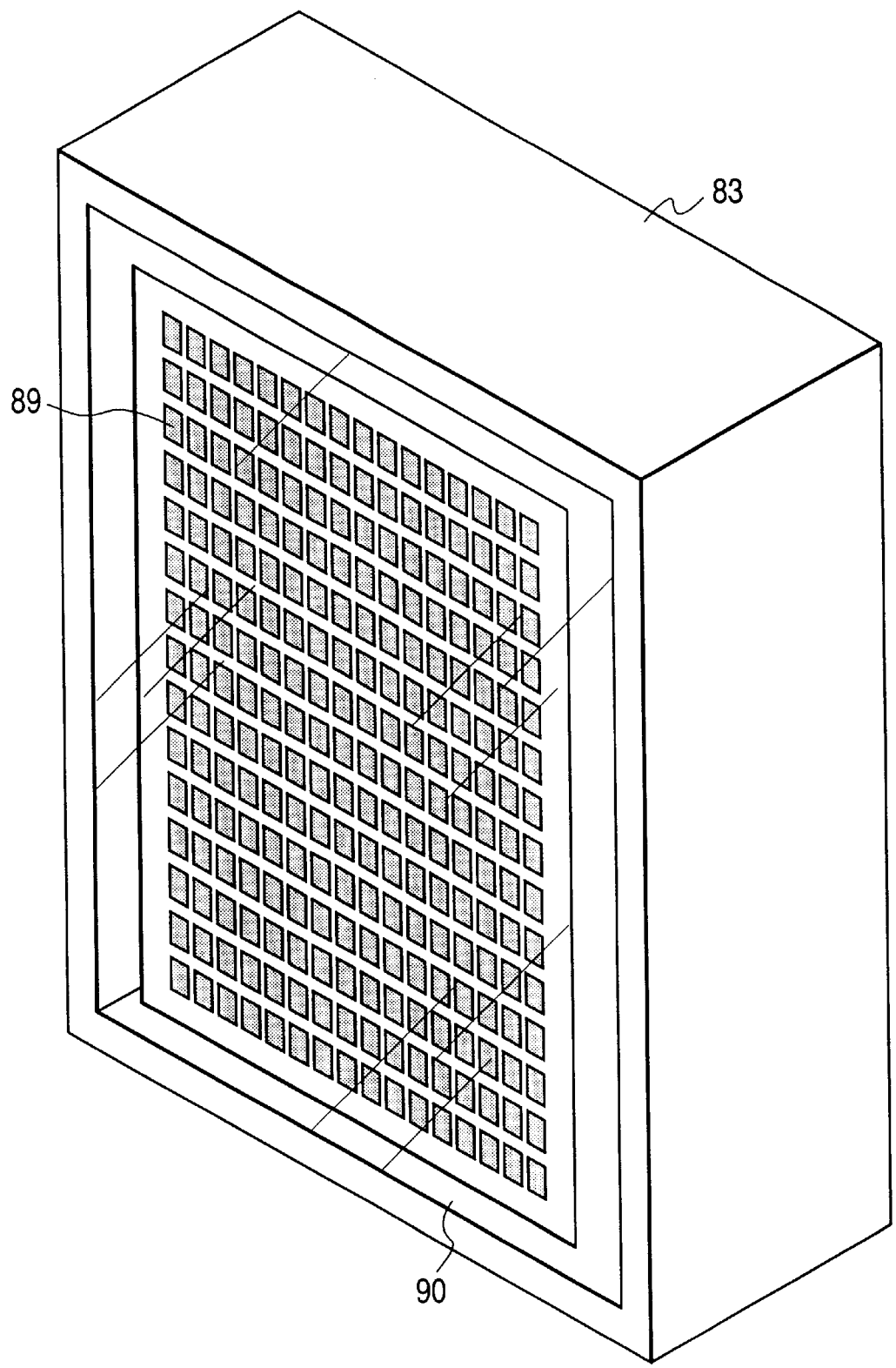
FIG. 39 is a perspective view of a radiographic unit using a plurality of photoelectric conversion elements.
Figure 40:
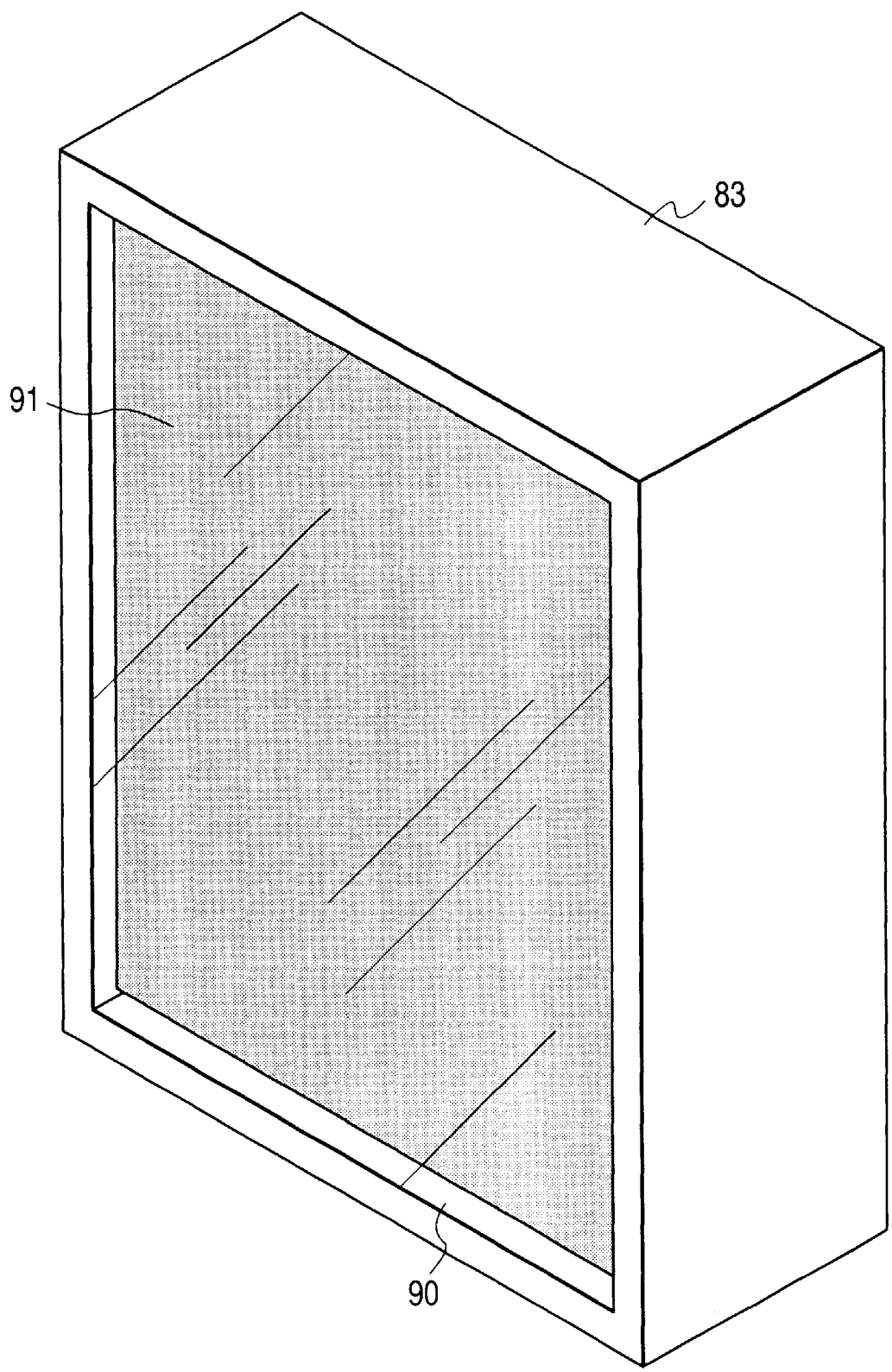
FIG. 40 is a perspective view of a radiographic unit using a photodetection array.
Figure 41:
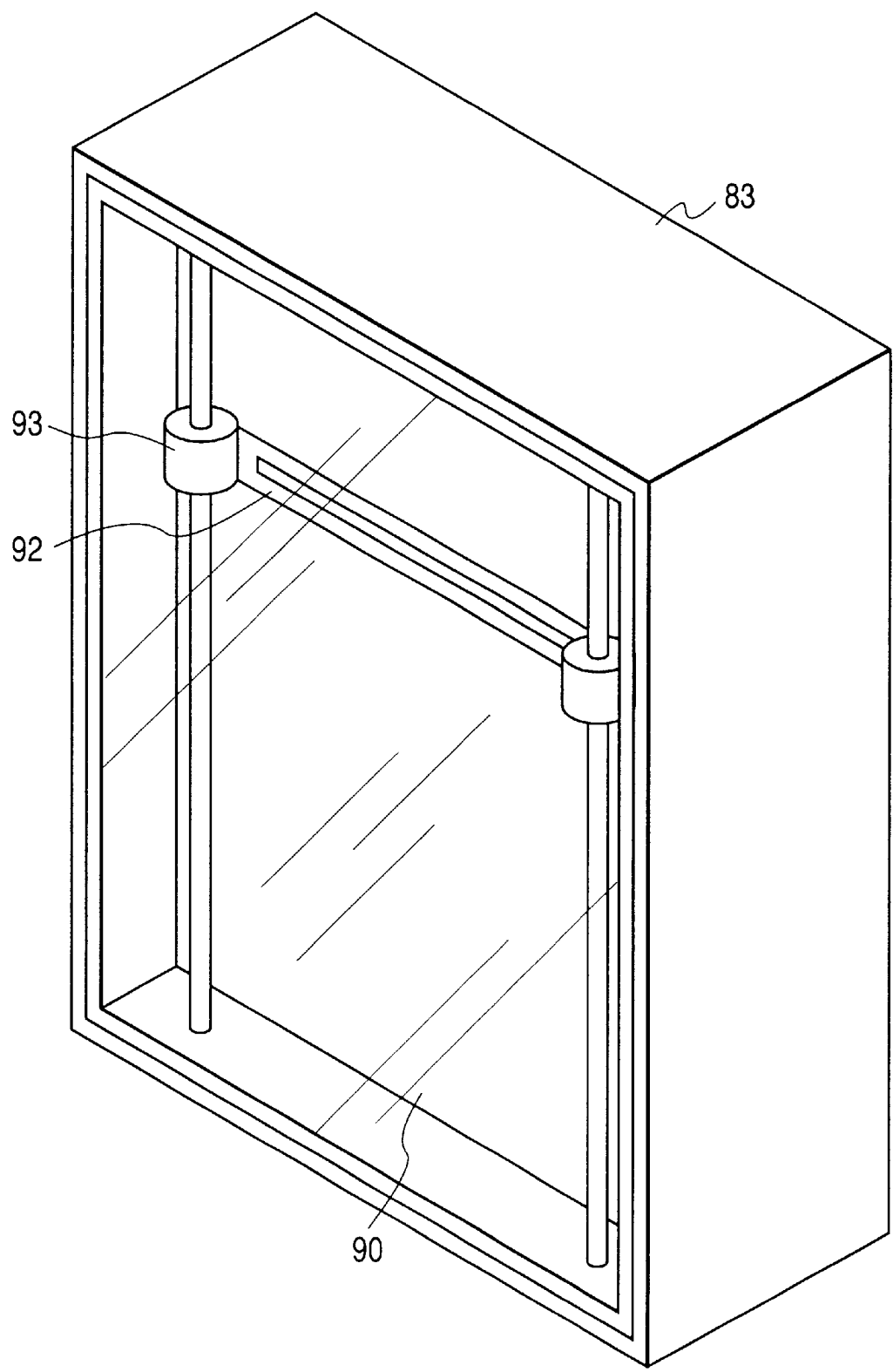
FIG. 41 is a perspective view of a radiographic unit using a line sensor and its drive means.

FIGS. 39 to 43 are perspective views of the object information acquiring means 88. FIG. 39 shows the object information acquiring means 88 made up of a plurality of photoelectric conversion elements 89 as semiconductor elements of, e.g., CdTe or the like. An object reception cover 90 which is transparent with respect to light is disposed in front of the object information acquiring means 88 so as to prevent the object S from directly touching the object information acquiring means 88. FIG. 40 shows the object information acquiring means 88 made up of a photodetection array 91 as a photoelectric conversion surface sensor of, e.g., amorphous silicon ($\alpha$Si) or the like. FIG. 41 shows the object information acquiring means 88 made up of a line sensor 92 as a linear photoelectric conversion element and a drive means 93. By driving the line sensor 92 in a direction perpendicular to its scanning direction, two-dimensional information of the object S can be acquired. The drive means 93 in this case comprises guide drive screws and a drive motor, and the line sensor 92 is retracted outside the irradiation region of radiation during irradiation.

Figure 42:
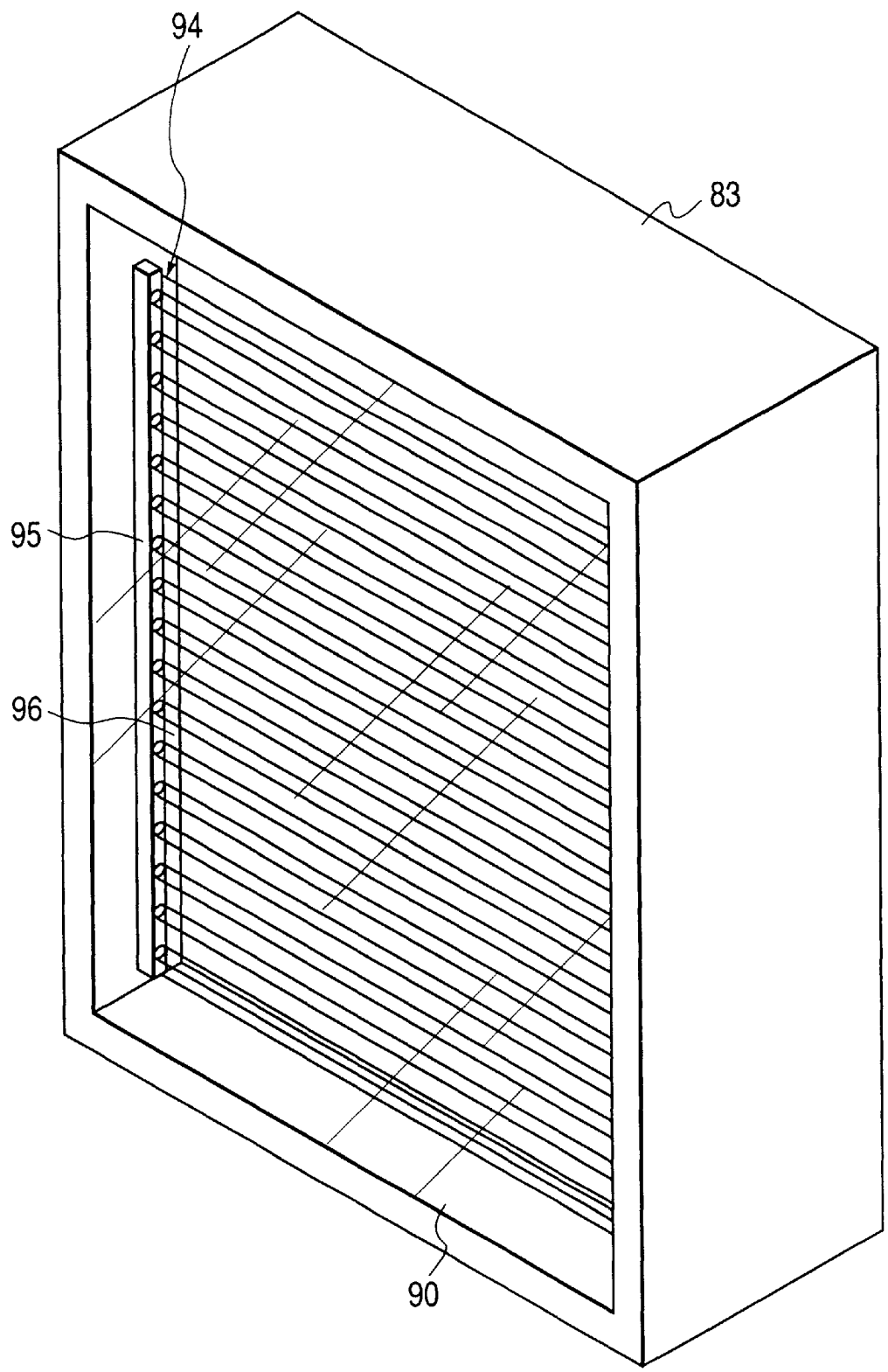
FIG. 42 is a perspective view of a radiographic unit using a light transmission means and line sensor.

Furthermore, FIG. 42 shows the object information acquiring means 88 made up of a light transmission means 94, and a line sensor 95 as a linear photoelectric conversion element. In this case, the line sensor 95 is attached to the end face of the light transmission means 94 to efficiently receive light coming from the light transmission means 94. The light transmission means 94 is constituted by stacking rods 96 consisting of a material having uniform radiation absorbency such as an acrylic resin in correspondence with the number of pixels of the line sensor 95, and these stacked rods 96 have different light incident positions to obtain two-dimensional information of the object S in accordance with the light incidence pattern.

Figure 43:
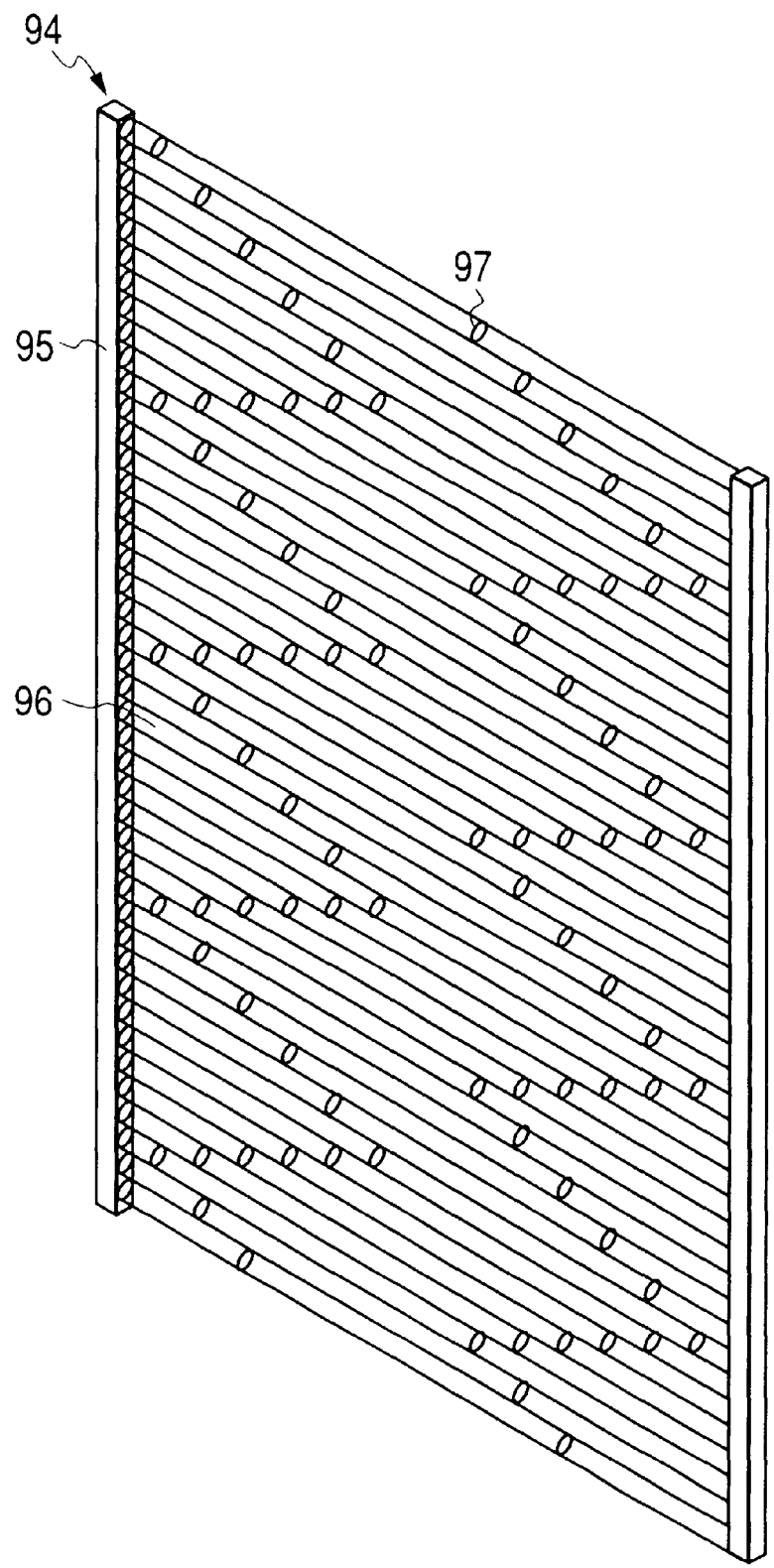
FIG. 43 is a perspective view of the light transmission means.

FIG. 43 is a perspective view of the light transmission means 94. Each rod 96 is divided into two pieces to intercept transmission of light, and has opening portions 97 that receive light. Line sensors 97 as linear photoelectric conversion elements are attached to the two end faces of the light transmission means 94, thus obtaining a double information amount.

Such object information acquiring means 88 can obtain two-dimensional information of the object S on the basis of the silhouette image of the object S or the presence/absence of incoming light when the light is intercepted by the object S. When the light source 84 that emits visible light or infrared light shown in FIG. 38 is turned on, two-dimensional information of the object S can be obtained more clearly. On the other hand, when a marginal light correction means for correcting the influences of marginal light and ambient light other than illumination light coming from the light source 84 is used, two-dimensional information of the object S can be obtained further clearly by subtracting the marginal light information obtained by the object information acquiring means 88 when the light source 84 is OFF from the incoming light information obtained by the object information acquiring means 88 when the light source 84 is ON.

In this manner, since the object information acquiring means 88 uses visible light or infrared light, it is not harmful to the human body. Also, when visible information acquired by the object information acquiring means 88, e.g., the silhouette image, is displayed on a television monitor, remote control is also allowed.

Figure 44:
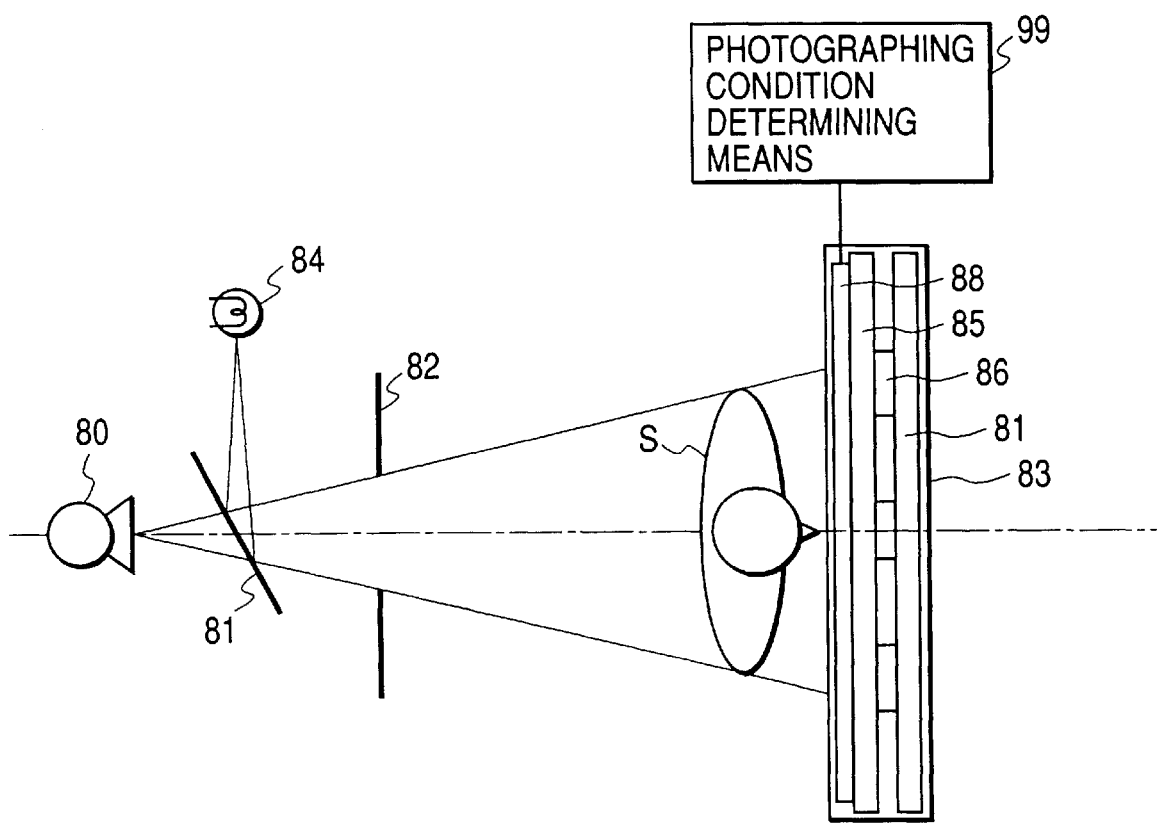
FIG. 44 is a view showing the arrangement according to the eighth embodiment of the present invention.

FIG. 44 shows the arrangement of a radiographic apparatus according to the eighth embodiment of the present invention. A photographing condition determining means 99 for determining the photographing conditions on the basis of two-dimensional information of the object S obtained by the object information acquiring means 88 is added to the radiographic apparatus of the seventh embodiment.

The photographing condition determining means 99 determines the photographing conditions on the basis of the two-dimensional information of the object S in the following order.

(1) The means 99 determines the posture, i.e., the front or side shot of the object S, and determines the quality of radiation, i.e., the radiation tube voltage.

(2) The means 99 determines the portion of the object S and determines the quality of radiation.

(3) The means 99 determines the irradiation range and determines the aperture range of the movable aperture stop 82.

(4) The means 99 determines the photographing range of the object S.

(5) The means 99 determines the effective region of the photo-timer light-receiving unit 86.

(6) The means 99 determines the gain of a photo-timer.

(7) The means 99 determines the read range when radiographic image information is read out from the radiographic image photographing means 97.

(8) The means 99 determines the process parameters used when the radiographic image information read out from the radiographic image photographing means 97 is subjected to an image process.

(9) The means 99 determines the size of a film used for outputting the radiographic image information via a laser printer or the like.

In this manner, since the photographing condition determining means 99 uses the two-dimensional information of the object S, the influences of blurring caused by scattered radiation of the radiographic image information can be removed, and processes such as edge extraction and the like can be easily done. Hence, the photographing conditions can be determined appropriately.

In the seventh and eighth embodiments described above, the two-dimensional information of the object S required for setting the quality and dose of the radiation generating means 80, setting the movable aperture stop 82, and setting image process parameters of a radiographic image for edge extraction and the like of the object S can be easily acquired, and the photographing conditions such as the quality and dose of the radiation generating means 80, setup of the movable aperture stop 82, and the like can be accurately and easily determined on the basis of the acquired two-dimensional information of the object S.

Figure 45:
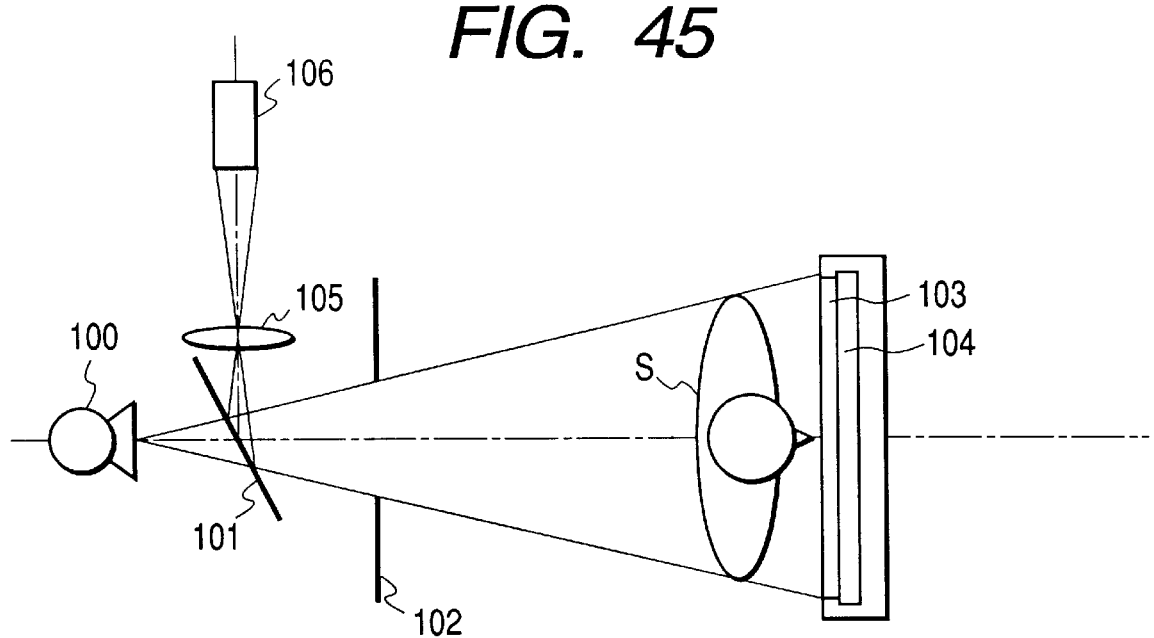
FIG. 45 is a view showing the arrangement according to the ninth embodiment of the present invention.

FIG. 45 shows the arrangement according to the ninth embodiment of the present invention. A return mirror 101 having high transmittance characteristics with respect to X-rays, movable aperture stop 102, object S, and radiographic means 104 having a photo-timer light-receiving unit 103 are disposed in turn in front of an X-ray tube 100 for emitting X-rays, and an imaging lens 105 and CCD camera 106 are disposed in the reflecting direction of the return mirror 101. When this radiographic apparatus photographs an image of the breast portion of the human body as the object S, and acquires object information useful for medical purposes from the photographed image, optimal conditions of the field of irradiation can be automatically set.

The X-ray tube 100 emits radiation toward the object S, and the radiographic means 104 obtains an image of the radiation intensity distribution transmitted through the object S. The photo-timer light-receiving unit 103 performs radiation input suitable for the photographing apparatus sensitivity characteristics, and prevents abnormal breast exposure. That is, the unit 103 transmits an irradiation stop signal to a controller of the X-ray tube 100 upon detecting a dose optimal for photographing. The movable aperture stop 102 intercepts irradiation onto an ineffective region in breast radiography, and avoids operation errors of the phototimer light-receiving unit 103 and irradiation excessive for radiography. On the other hand, the CCD camera 106 observes a visible object image via the imaging lens 105 and return mirror 101 so as to obtain object position information without any irradiation.

Figure 46:
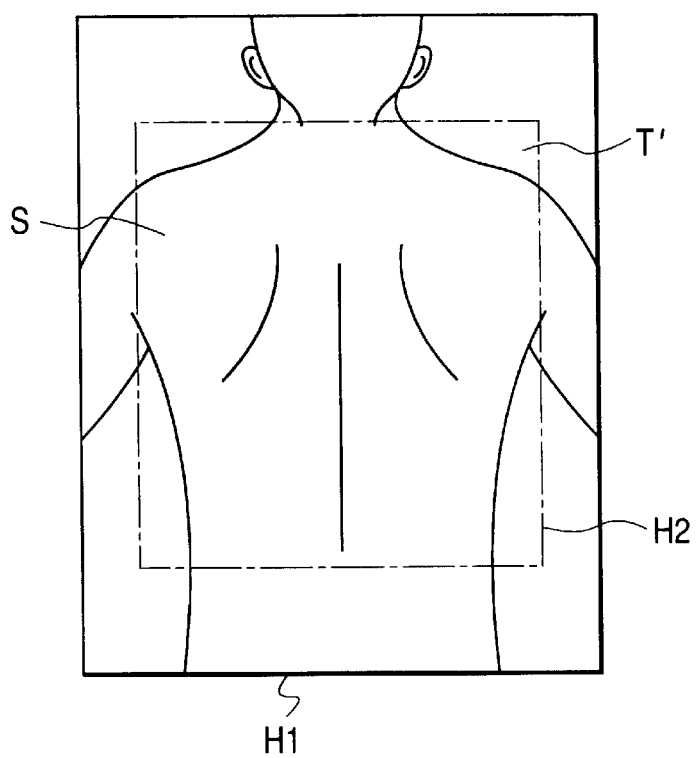
FIG. 46 is an explanatory view of object position information.
Figure 47A:
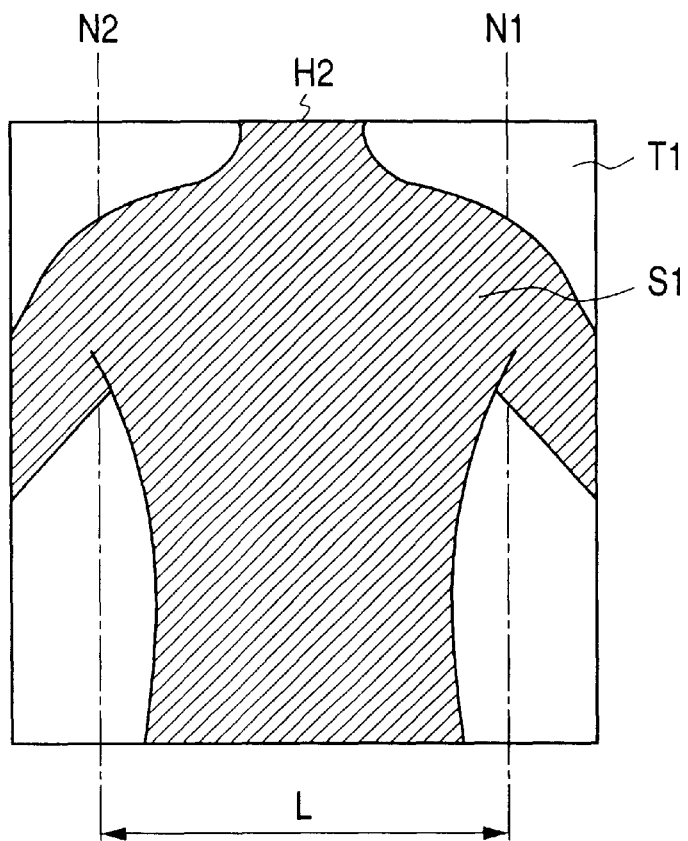
FIGS. 47A and 47B are explanatory views of an object region information process method.

In order to determine the effective field of irradiation and to automatically set optimal conditions of the actual field of irradiation in radiography, i.e., actual photographing, the CCD camera 106 photographs an object image before the actual photographing, and acquires object position information based on an object image S' shown in FIG. 46. An actual photographing image receiving region H2 obtained when the movable aperture stop 102 is fully open is present inside a photographing region Hi of the CCD camera 106, and a background image T' is present on the background of the object image S'. The background image T' preferably has a color tone different from that of the object image S' in correspondence with the light-receiving characteristics of the CCD camera 106 so that it can be easily distinguished from the object image S', and the object region can be accurately and easily extracted. An object region extraction means which binarizes the object image S' and background image T' in the actual photographing image receiving region H2 from the object position information on the basis of the color tone or the like extracts an object region S1, as shown in FIG. 47A.

Figure 47B:
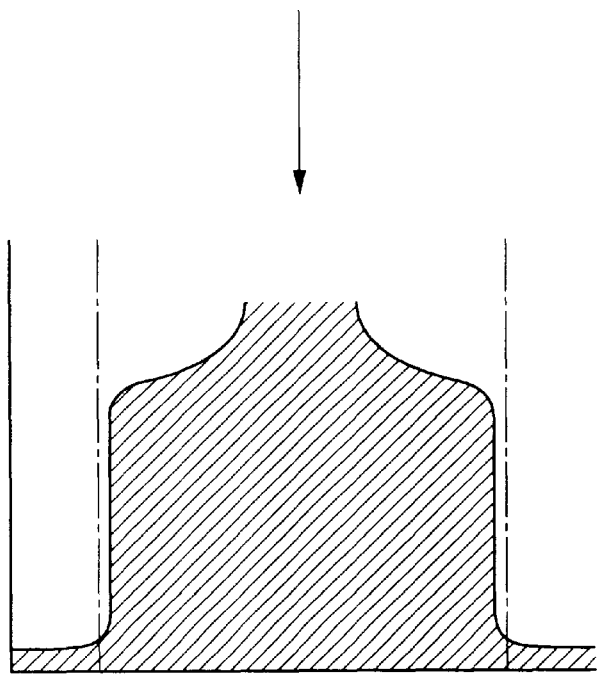

Subsequently, using an optimal photographing condition determining means, a proper irradiation field determining means in a breast shot in case of this embodiment, a proper field L of irradiation in actual photographing is determined. By accumulating the object region S1 extracted from the front shot image in the vertical direction, a histogram is generated, as shown in FIG. 47B, and arm regions with smaller distributions in the vertical direction are determined to identify the breast portion. However, in an object S with no arm portions like in a side shot image, this procedure is omitted. In correspondence with the width of the remaining breast portion, an optimal target field L of irradiation is determined as indicated by movable aperture stop edges N1 and N2 in FIG. 47A.

Finally, the movable aperture stop 102 is automatically set to complete preparation for actual photographing. When the photographer does not want to perform automatic setting, the optimal field L of irradiation may be compared with the current irradiation state to determine the degree of mismatch using a threshold value, and the determination result may be displayed as a warning message.

In this embodiment, the object position information acquiring means uses the CCD camera 106 and imaging lens 105. In place of the CCD camera 106, a two-dimensional image sensing tube may be used. On the other hand, the optical axis of radiation agrees with that of the object position information acquiring means, but they need not agree with each other as long as the actual photographing image receiving position is appropriately calibrated. Furthermore, the object position information acquiring means may obtain the intensity distribution on a photographing surface by means of laser scanning and a photosensor for receiving the reflected laser beam, or may receive the projected object distribution by means of existing illumination, and an optical fiber array and photosensor arranged in front of the photographing surface. In this embodiment, the movable aperture stop 102 is movable in only the horizontal direction. However, in order to protect the head and abdomen portions, the movable aperture 102 may also be disposed in the vertical direction.

As described above, in the ninth embodiment, the object region S1 can be easily and accurately extracted immediately before actual photographing, and optimal photographing conditions in actual photographing are automatically set and indicated, thus preventing actual photographing errors under improper photographing conditions. The object region S1 can be extracted immediately before actual photographing, and the field of irradiation optimal to actual photographing can be automatically set and indicated to the photographer. Furthermore, the effective region of the photo-timer light-receiving unit 103 can be determined based on the object region S1. Also, the posture of the object S in front or side shot is determined based on the object region S1, and the gain of the photo-timer can be determined in correspondence with the determined posture. Moreover, by comparing the object region S1 with a look-up table prepared in advance, the photographing portion can be determined, and the tube voltage corresponding to the photographing portion can be automatically set and indicated to the photographer. Hence, actual photographing errors due to an insufficient exposure amount can be prevented.

In order to prevent operation errors under the influences of unintercepted radiation, a radiographic apparatus which automatically sets optimal conditions of the photo-timer light-receiving region may be used. In this case, the object position information acquiring means and object region extraction means of the ninth embodiment are used to extract the edge of the breast portion of the object. Using an optimal condition determining means which does not use any portion other than the object region within the light-receiving region of the photo-timer light-receiving unit 103, weights the light-receiving region, or the like, the effective region of the photo-timer in actual photographing is determined and is automatically set.

In order to correct the difference in scattered radiation in front and side shots, the photo-timer gain may be automatically switched. The object position information acquiring means and object region extraction means of the ninth embodiment are used to extract the edge of the breast portion of the object. By determining the width, symmetry, and presence/absence of arm portions of the object S using a threshold value, a front or side shot is determined, and the photo-timer gain is switched to a prescribed value for the front or side shot. In order to prevent determination errors, the determination result may be merely indicated to the photographer using a display means.

Furthermore, the quality of radiation that optimizes the object contrast in the radiographic image depending on the photographing portion may be automatically set. In this case, radiation quality adjustment is substantially determined by the tube voltage of the X-ray tube 100. The object region is extracted using the object position information acquiring means and object region extraction means of the ninth embodiment, and is compared with head, breast, abdomen, hand, and leg photographing portion look-up tables, which are prepared in advance by pattern matching, thus determining the photographing portion. Recommended tube voltage look-up tables prepared in units of portions are looked up for the determined portion, and the tube voltage for actual photographing is automatically set or is displayed as a recommended tube voltage.

What is claimed is:

1. A radiographic apparatus comprising:
   a radiographing unit for radiographing an object irradiated with radiation and obtaining radiographic image data;
   an object information detecting unit for detecting a light image of the object and obtaining light image data;
   an image processing unit for performing an image processing of said radiographic image data obtained by said radiographing unit and outputting processed radiographic image data;
   a determination unit for determining an image processing condition used by said image processing unit on the basis of said light image data obtained by said object information detecting unit.

2. An apparatus according to claim 1, further comprising a unit for indicating object information obtained by said object information detecting unit.

3. An apparatus according to claim 1, further comprising a unit for determining a radiographing condition on the basis of said light image data obtained by said object information detecting unit.

4. An apparatus according to claim 1, wherein said object information detecting unit detects a visible light image of the object as the light image.

5. An apparatus according to claim 1, further comprising a unit for determining location of the object on the basis of said light image data obtained by said object information detecting unit.

6. A radiographic apparatus comprising:
   a radiographing unit for radiographing an object irradiated with radiation and obtaining radiographic image data;
   an object information detecting unit for detecting a light image of the object and obtaining light image data; and
   a body part specifying unit for specifying a part of the object to be radiographed by said radiographing unit on the basis of said light image data obtained by said object information detecting unit.

7. An apparatus according to claim 6, further comprising a unit for determining a radiographing condition for radiographing the object on the basis of body part information obtained by said body part specifying unit.

8. An apparatus according to claim 6, further comprising a unit for determining a condition for an image processing of radiographic image data obtained by said radiographing unit on the basis of body part information obtained by said body part specifying unit.

9. A radiographic apparatus comprising:
   a radiographing unit for radiographing an object irradiated with radiation and obtaining radiographic image data;
   an object information detecting unit for detecting a light image of the object and obtaining light image data; and
   a posture specifying unit for specifying posture of the object on the basis of said light image data obtained by said object information detecting unit.

10. An apparatus according to claim 7, further comprising a unit for determining a radiographing condition for radiographing the object on the basis of posture information obtained by said posture specifying unit.

11. An apparatus according to claim 9, further comprising a unit for determining a condition for an image processing of radiographic image data obtained by said radiographing unit on the basis of posture information obtained by said posture specifying unit.

12. A radiographic apparatus comprising:
    a radiographing unit for radiographing an object irradiated with radiation and obtaining radiographic image data;
    an object information detecting unit for detecting a light image of the object and obtaining light image data;
    a determination unit for determining an irradiation field region in said radiographic image data obtained by said radiographing unit on the basis of said light image data obtained by said object information detecting unit; and
    an image processing unit for performing an image processing of said irradiation field region, determined by said determination unit in said radiographic image data and outputting processed radiographic image data.

13. A radiographic apparatus according to claim 12, further comprising a position correspondence unit for making positional correspondence between said radiographic image data and said light image data.

* * * * *

UNITED STATES PATENT AND TRADEMARK OFFICE
CERTIFICATE OF CORRECTION

PATENT NO. : 6,502,984 B2
DATED : January 7, 2003
INVENTOR(S) : Ogura et al.

It is certified that error appears in the above-identified patent and that said Letters Patent is hereby corrected as shown below:

<u>Title page,</u>
Item [56], References Cited, U.S. PATENT DOCUMENTS, "Otsuke et al." should read -- Otsuki et al. --.

<u>Column 22,</u>
Line 38, "Claim 7" should read -- Claim 9 --.

Signed and Sealed this

Eleventh Day of November, 2003

JAMES E. ROGAN
*Director of the United States Patent and Trademark Office*